United States Patent
Homma et al.

(10) Patent No.: US 12,007,348 B2
(45) Date of Patent: Jun. 11, 2024

(54) METHOD FOR DRIVING GAS SENSOR, AND GAS DETECTION DEVICE

(71) Applicant: Nuvoton Technology Corporation Japan, Kyoto (JP)

(72) Inventors: Kazunari Homma, Gifu (JP); Koji Katayama, Nara (JP); Shunsaku Muraoka, Osaka (JP); Ken Kawai, Osaka (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 288 days.

(21) Appl. No.: 17/496,468

(22) Filed: Oct. 7, 2021

(65) Prior Publication Data
US 2022/0026384 A1    Jan. 27, 2022

Related U.S. Application Data

(63) Continuation of application No. PCT/JP2020/002233, filed on Jan. 23, 2020.

(30) Foreign Application Priority Data

Apr. 16, 2019  (JP) .................................. 2019-078029

(51) Int. Cl.
G01N 27/12    (2006.01)
G01N 33/00    (2006.01)
(Continued)

(52) U.S. Cl.
CPC .......... G01N 27/125 (2013.01); G01N 33/005 (2013.01); G01R 19/0092 (2013.01);
(Continued)

(58) Field of Classification Search
CPC .... G01N 27/125; G01N 33/005; G01N 27/12; G01R 27/02; G01R 19/0092;
(Continued)

(56) References Cited

U.S. PATENT DOCUMENTS

2004/0231974 A1* 11/2004 Bottner ................ G01N 27/125
                                                    427/255.31
2009/0090169 A1*  4/2009 Hara .................... G01N 27/125
                                                    73/31.05
(Continued)

FOREIGN PATENT DOCUMENTS

WO    2018/123673 A1    7/2018
WO    2018/123674 A1    7/2018

OTHER PUBLICATIONS

WO 2018/123674 Machine Translation, Jul. 5, 2018 (Year: 2018).*
(Continued)

*Primary Examiner* — Raul J Rios Russo
(74) *Attorney, Agent, or Firm* — Rimon P.C.

(57) ABSTRACT

A gas sensor driving method for a gas sensor that (i) includes: a first electrode including a first principal surface; a second electrode including a second principal surface; a metal-oxide layer interposed between the first principal surface and the second principal surface that face each other; and an insulating film covering the first electrode, the metal-oxide layer, and the second electrode, and exposing at least a part of a third principal surface of the second electrode, the third principal surface being disposed on an opposite side of the second principal surface, and (ii) detects hydrogen in accordance with a change in a resistance value of the metal-oxide layer. The gas sensor driving method includes repeatedly applying a positive voltage and a negative voltage across the first electrode and the second electrode.

15 Claims, 21 Drawing Sheets

(51) Int. Cl.
*G01R 19/00* (2006.01)
*G01R 27/02* (2006.01)
*G01R 27/14* (2006.01)
*H01L 21/66* (2006.01)

(52) U.S. Cl.
CPC ............. *G01R 27/02* (2013.01); *G01R 27/14* (2013.01); *H01L 22/34* (2013.01); *H01L 2924/00* (2013.01); *H01L 2924/0002* (2013.01)

(58) Field of Classification Search
CPC ................ G01R 27/14; H01L 2924/00; H01L 2924/0002; H01L 22/34
USPC .......................................................... 324/713
See application file for complete search history.

(56) References Cited

U.S. PATENT DOCUMENTS

| | | | | |
|---|---|---|---|---|
| 2012/0307557 | A1* | 12/2012 | Itagaki | G11C 16/14 365/185.02 |
| 2017/0241933 | A1* | 8/2017 | Fujii | G01N 33/005 |
| 2019/0383690 | A1* | 12/2019 | Muraoka | H01M 8/04089 |
| 2020/0096465 | A1* | 3/2020 | Kawai | B60L 50/71 |

OTHER PUBLICATIONS

International Search Report and Written Opinion issued on Apr. 7, 2020 in International Patent Application No. PCT/JP2020/002233; with partial English translation.

\* cited by examiner

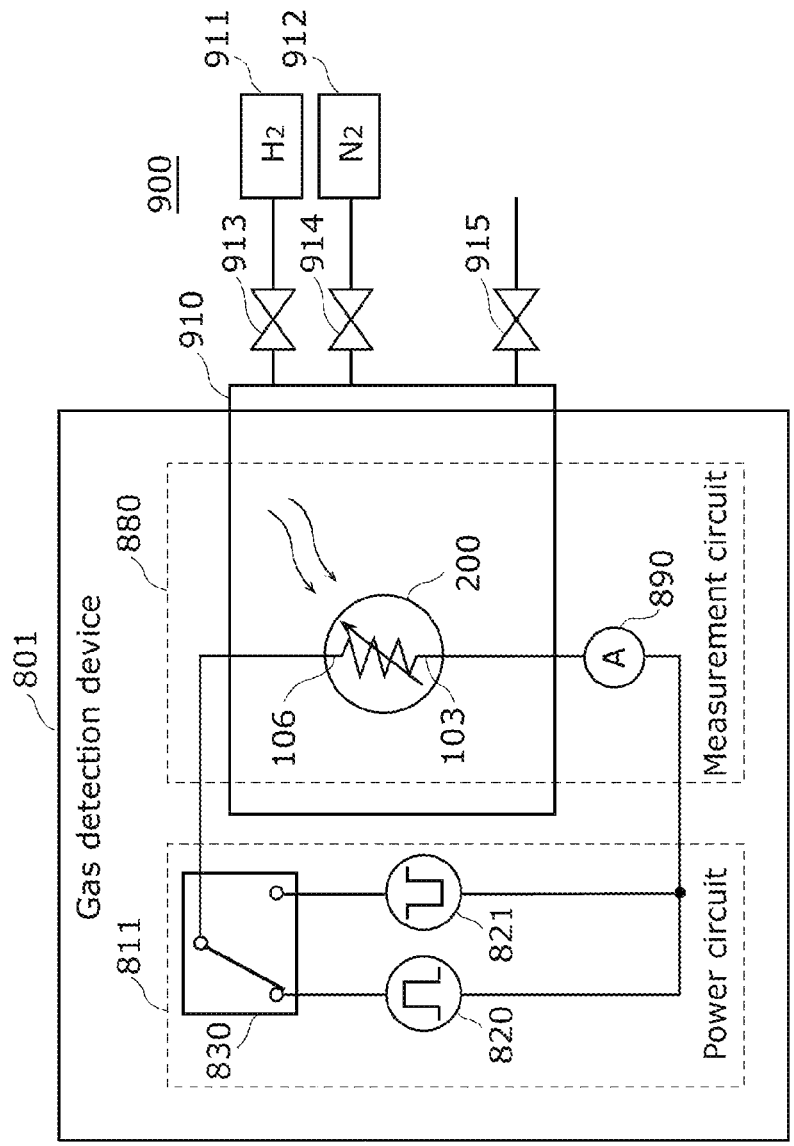

METHOD FOR DRIVING GAS SENSOR, AND GAS DETECTION DEVICE

CROSS REFERENCE TO RELATED APPLICATIONS

This is a continuation application of PCT International Application No. PCT/JP2020/002233 filed on Jan. 23, 2020, designating the United States of America, which is based on and claims priority of Japanese Patent Application No. 2019-078029 filed on Apr. 16, 2019. The entire disclosures of the above-identified applications, including this specifications, drawings and claims are incorporated herein by reference in their entirety.

FIELD

The present disclosure relates to a method for driving a gas sensor, and a gas detection device.

BACKGROUND

A gas detection device that detects gas including gas molecules containing hydrogen atoms (hereinafter referred to as hydrogen-containing gas), using a gas sensor in which a first electrode, a metal-oxide layer, and a second electrode are stacked is conventionally known (for example, see PTL 1).

The gas detection device according to PTL 1 detects hydrogen-containing gas, utilizing the nature of a gas sensor that when part of the second electrode contacts hydrogen-containing gas in a state in which a voltage is applied across the first electrode and the second electrode, the resistance value of the metal-oxide layer decreases. The resistance value of the metal-oxide layer is measured based on the value of a read current that flows when a predetermined voltage is applied across the first electrode and the second electrode.

The resistance value of the metal-oxide layer which has decreased due to contact with hydrogen-containing gas may not return, even after the hydrogen-containing gas is no longer present, to the previous value held before the contact with hydrogen-containing gas. In view of this, when the read current exceeds a predetermined threshold, the gas detection device according to PTL 1 applies a reset voltage across the first electrode and the second electrode to reset the resistance value of the metal-oxide layer to the previous value held before the contact with hydrogen-containing gas.

The gas detection device according to PTL 1 thus achieves stable detection of hydrogen-containing gas by electrically resetting the resistance value of the metal-oxide layer.

CITATION LIST

Patent Literature

PTL 1: International Publication No. WO2018/123673

SUMMARY

Technical Problem

The gas detection device according to PTL 1 makes a comparative judgment of comparing the value of a read current with a predetermined threshold, and electrically resets the resistance value of the metal-oxide layer in accordance with the judgment result. The resetting procedure therefore easily gets complicated.

In view of this, the present disclosure provides a method for driving a gas sensor, and a gas detection device which enable the resetting of the resistance value of a metal-oxide layer with a simple procedure.

Solution to Problem

A gas sensor driving method according to an aspect of the present disclosure is a gas sensor driving method for a gas sensor that (i) includes: a first electrode including a first principal surface; a second electrode including a second principal surface; a metal-oxide layer interposed between the first principal surface and the second principal surface that face each other; and an insulating film covering the first electrode, the metal-oxide layer, and the second electrode, and exposing at least a part of a third principal surface of the second electrode, the third principal surface being disposed on an opposite side of the second principal surface, and (ii) detects hydrogen in accordance with a change in a resistance value of the metal-oxide layer occurring when the part of the third principal surface contacts gas including gas molecules containing hydrogen atoms in a state in which a voltage is applied across the first electrode and the second electrode. The gas sensor driving method includes repeatedly applying a positive voltage and a negative voltage across the first electrode and the second electrode.

A gas detection device according to an aspect of the present disclosure includes: a gas sensor that includes a first electrode including a first principal surface, a second electrode including a second principal surface, a metal-oxide layer interposed between the first principal surface and the second principal surface that face each other, an insulating film covering the first electrode, the metal-oxide layer, and the second electrode, and exposing at least a part of a third principal surface of the second electrode, the third principal surface being disposed on an opposite side of the second principal surface; and a power circuit that repeatedly applies a positive voltage and a negative voltage across the first electrode and the second electrode in the gas sensor.

Advantageous Effects

With the gas sensor driving method or the gas detection device according to an aspect of the present disclosure, a positive voltage and a negative voltage are repeatedly applied across the first electrode and the second electrode. Accordingly, it is possible to repeat the reading and resetting of the resistance value of the metal-oxide layer with a simple procedure that does not require any conditional judgment.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 9 is a functional block diagram illustrating an example of a configuration of a gas detection device according to Embodiment 1.

DESCRIPTION OF EMBODIMENTS

Figure 1A:
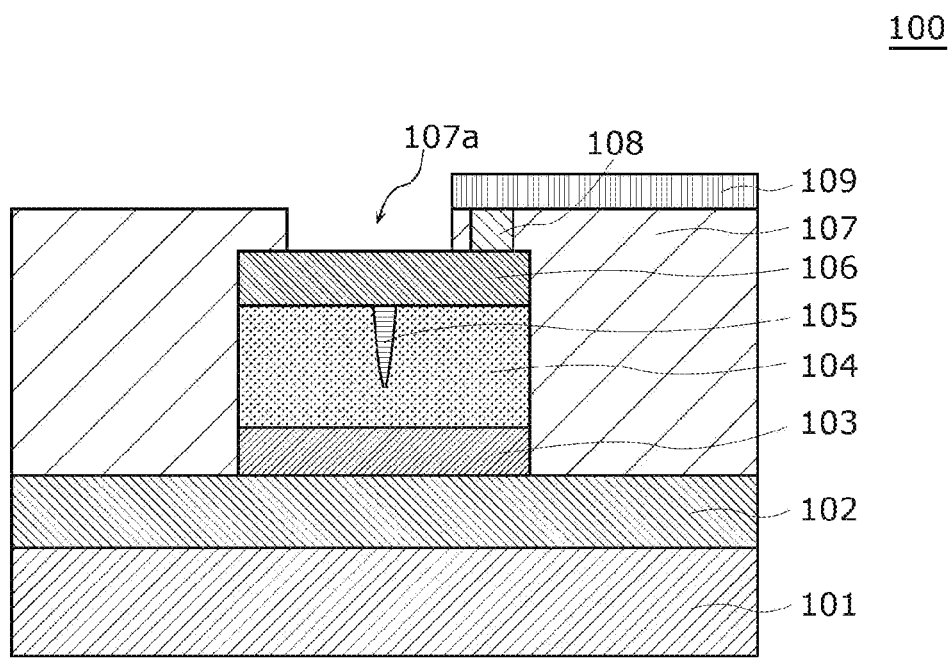
FIG. 1A is a cross-sectional view illustrating an example of a structure of a gas sensor according to an embodiment.

Hereinafter, embodiments of the present disclosure will be described with reference to the drawings.

Note that structural elements with substantially same configurations, operations, and effects are assigned with like reference signs in the drawings, and description is omitted. Moreover, numerical values, materials, compositions, shapes, film formation methods, the connection of structural elements, etc. described in the following embodiments are mere examples for specifically illustrating the embodiments of the present disclosure, and the present disclosure is not limited to these examples. Among structural elements described in the following embodiments, those not recited in any one of the independent claims that indicate the broadest concepts are described as optional structural elements.

[Configuration of Gas Sensor]

A gas sensor according to an embodiment has a metal-insulator-metal (MIM) structure in which a resistive film (metal-oxide layer) and metal films are stacked. By utilizing self-heating and gas sensitivity in a local region formed in the resistive film, the gas sensor can detect hydrogen-containing gas without having to heat up the gas sensor with a heater. Hydrogen-containing gas here is a general term for any gas including molecules with hydrogen atoms, and, to give an example, can include hydrogen, methane, alcohol, etc.

FIG. 1A is a cross-sectional view illustrating an example of a structure of gas sensor 100 according to the embodiment.

Figure 1B:
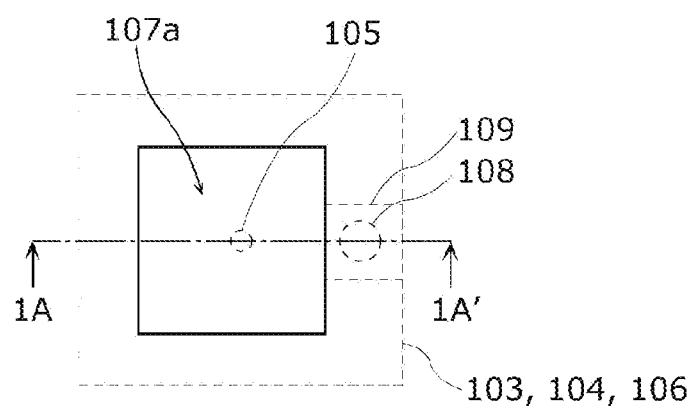
FIG. 1B is a top view illustrating an example of the structure of the gas sensor according to the embodiment.

FIG. 1B is a top view illustrating an example of the structure of gas sensor 100 according to the embodiment. The cross section in FIG. 1A corresponds to a cross section taken along line 1A-1A' in FIG. 1B and viewed along the arrows.

Gas sensor 100 includes substrate 101, insulating film 102 formed on substrate 101, first electrode 103 formed on insulating film 102, second electrode 106, metal-oxide layer 104 interposed between first electrode 103 and second electrode 106, insulating film 107, via 108, and wiring 109. A first principal surface of first electrode 103 and a second principal surface of second electrode 106 are disposed facing each other, and metal-oxide layer 104 is interposed between the first principal surface of first electrode 103 and the second principal surface of second electrode 106.

Insulating film 107 is provided with aperture 107a for allowing second electrode 106 to contact gas which is an inspection target. Stated differently, insulating film 107 covers first electrode 103, second electrode 106, and metal-oxide layer 104 while at least a part of a third principal surface of second electrode 106 (the other principal surface on an opposite side of the second principal surface) is exposed without being covered by insulating film 107.

Metal-oxide layer 104 is interposed between first electrode 103 and second electrode 106. The resistance value of metal-oxide layer 104 reversibly changes based on an electric signal given between first electrode 103 and second electrode 106. For example, the resistive state of metal-oxide layer 104 transitions reversibly between a high-resistance state and a low-resistance state in accordance with a voltage (a potential difference) given between first electrode 103 and second electrode 106. The resistive state of metal-oxide layer 104 transitions, for example, from a high-resistance state to a low-resistance state in accordance with hydrogen-containing gas that has contacted second electrode 106.

Metal-oxide layer 104 includes, inside, local region 105 that is disposed in contact with second electrode 106 and is not contacting first electrode 103. The oxygen deficiency degree of local region 105 is higher than that of the surrounding area (i.e., a bulk region in metal-oxide layer 104).

The oxygen deficiency degree of local region 105 reversibly changes in accordance with (i) the application of an electric signal between first electrode 103 and second electrode 106 and (ii) a presence of hydrogen-containing gas in the gas that second electrode 106 contacts. Local region 105 is a minute region that includes a filament (conductive path) composed of oxygen defect sites.

Via 108 penetrates insulating film 107 and is thus connected to second electrode 106 in a portion of insulating film 107 which covers the upper surface of second electrode 106. Wiring 109 is disposed above via 108.

Note that in the present disclosure, the "oxygen deficiency degree" of a metal oxide refers to a ratio of an oxygen deficiency amount in the metal oxide to the amount of oxygen in a stoichiometric compositional oxide made up of the same chemical elements as the metal oxide (the oxygen deficiency amount here is a value obtained by subtracting the amount of oxygen in a stoichiometric compositional metal oxide from the amount of oxygen in the metal oxide). If there are stoichiometric compositional metal oxides each being made up of the same chemical elements as the metal oxide, the oxygen deficiency degree of the metal oxide is defined based on one of the stoichiometric compositional metal oxides which has the highest resistance value. The stoichiometric compositional metal oxide is more stable and has a higher resistance value than a metal oxide with another composition.

When the metal is tantalum (Ta), for example, the stoichiometric compositional oxide according to the above-mentioned definition can be expressed as $TaO_{2.5}$ since the composition thereof is $Ta_2O_5$. The oxygen deficiency degree of $TaO_{2.5}$ is 0%, and the oxygen deficiency degree of $TaO_{1.5}$ is derived by $(2.5-1.5)/2.5=40\%$. A metal oxide with too much oxygen has an oxygen deficiency degree indicating a negative value. Note that in the present disclosure, the oxygen deficiency degree may take a positive value, 0, or a negative value unless otherwise noted.

An oxide with a low oxygen deficiency degree has a high resistance value since the oxide is closer to a stoichiometric compositional oxide, and an oxide with a high oxygen deficiency degree has a low resistance value since the oxide is closer to a metal composing an oxide.

The term "oxygen content" refers to the percentage of oxygen atoms in the total amount of atoms. For example, the oxygen content of $Ta_2O_5$ is the percentage of oxygen atoms in the total amount of atoms, which is derived by $(O/(Ta+O))$ resulting in 71.4 atm %. Accordingly, it is derived that the oxygen content of an oxygen-deficient tantalum oxide is greater than 0 and less than 71.4 atm %.

Local region 105 is formed in metal-oxide layer 104 by applying an initial break voltage across first electrode 103 and second electrode 106. Stated differently, the initial break voltage is a voltage applied across first electrode 103 and second electrode 106 in order to form local region 105. The absolute value of the initial break voltage may be larger than that of a write voltage. The write voltage is a voltage applied across first electrode 103 and second electrode 106 in order to cause metal-oxide layer 104 to reversibly transition between a high-resistance state and a low-resistance state. Alternatively, the absolute value of the initial break voltage may be smaller than that of a write voltage. In this case, the initial break voltage may be repeatedly applied, or continuously applied for a predetermined period of time. With the application of the initial break voltage, local region 105 that is in contact with second electrode 106 but not in contact with first electrode 103 is formed, as illustrated in FIG. 1A.

It is conceivable that local region 105 includes a filament (conductive path) composed of oxygen defect sites. Local region 105 has a minute size that matches the size of a filament necessary for a current to flow. The formation of the filament in local region 105 will be described using a percolation model.

The percolation model is based on a theory that assumes a random distribution of oxygen defect sites in local region 105, and the probability at which the connection of oxygen defect sites is formed increases if the density of the oxygen defect sites exceeds a threshold.

According to the percolation model, a filament is formed by a plurality of oxygen defect sites in local region 105 being connected, and a resistance change in metal-oxide layer 104 appears through the generation and disappearance of the oxygen defect sites in local region 105.

The term "oxygen deficiency" here means that oxygen is deficient in the stoichiometric composition of a metal oxide, and the term "the density of oxygen defect sites" is related to the oxygen deficiency degree. In other words, the density of oxygen defect sites increases as the oxygen deficiency degree gets higher.

Local region 105 may be formed in only one place in metal-oxide layer 104 of gas sensor 100. The number of local regions 105 formed in metal-oxide layer 104 can be confirmed, for example, through electron beam absorbed current (EBAC) analysis.

In the case where local region 105 is present in metal-oxide layer 104, a current in metal-oxide layer 104 flows intensively through local region 105 when a voltage is applied across first electrode 103 and second electrode 106.

The size of local region 105 is small. Therefore, local region 105 generates heat due to, for example, a current of approximately several tens of microamperes which flows when the resistance value of metal-oxide layer 104 is read out, and the heat generation causes a significant rise in temperature. When the current of approximately several tens of microamperes flows, the power consumption thereof is less than 0.1 mW, for example.

In view of this, second electrode 106 includes a metal, e.g., platinum (Pt), having a catalytic action, and local region 105 is connected to second electrode 106 and is thus formed. According to this configuration, second electrode 106 is heated by heat generation in local region 105 and hydrogen atoms are efficiently dissociated from hydrogen-containing gas.

When hydrogen-containing gas is present in the gas that is the inspection target, hydrogen atoms are dissociated from the hydrogen-containing gas in second electrode 106, and the dissociated hydrogen atoms are bonded with oxygen atoms in local region 105. As a result, the resistance value of local region 105 decreases.

In this way, gas sensor 100 has a feature that the resistance value across first electrode 103 and second electrode 106 decreases when second electrode 106 contacts hydrogen-containing gas. Owing to this feature, it is possible to detect hydrogen-containing gas in the gas that is the inspection target by detecting a reduction in the resistance value across first electrode 103 and second electrode 106 when the gas contacts second electrode 106.

Note that no matter which state local region 105 is in, either in a high-resistance state or in a low-resistance state, a reduction in the resistance value is caused by hydrogen-containing gas contacting second electrode 106. Therefore, hydrogen-containing gas can be detected by either gas sensor 100 including local region 105 that is in a high-resistance state or gas sensor 100 including local region 105 that is in a low-resistance state. However, in order to clearly detect a reduction in the resistance value, gas sensor 100 with local region 105 that is electrically set to a high-resistance state in advance may be used.

Hereinafter, the details of gas sensor 100 for obtaining stable resistance change characteristics will be described.

Metal-oxide layer 104 includes an oxygen-deficient metal oxide. At least one metal may be selected for the maternal metal of the metal oxide from among aluminum (Al) and transition metals such as tantalum, hafnium (Hf), titanium (Ti), zirconium (Zr), niobium (Nb), tungsten (W), nickel (Ni), and iron (Fe). Since a transition metal can take on a plurality of oxidization states, it is possible to achieve different resistive states through redox reactions.

An oxygen-deficient metal oxide has a higher oxygen deficiency degree compared to a stoichiometric compositional metal oxide containing identical metal elements. The stoichiometric compositional metal oxide is a typical insulator whereas the oxygen-deficient metal oxide has typical semiconducting properties. By using an oxygen-deficient metal oxide for metal-oxide layer 104, gas sensor 100 can achieve resistance change behaviors with good reproducibility and stability.

In the case of using a hafnium oxide as a metal oxide included in metal-oxide layer 104, for example, when x in $HfO_x$ representing the composition of the hafnium oxide is 1.6 or greater, it is possible to stably change the resistance value of metal-oxide layer 104. In this case, the film thickness of the hafnium oxide may be 3 nm to 4 nm.

In the case of using a zirconium oxide as the metal oxide included in metal-oxide layer 104, when x in $ZrO_x$ representing the composition of the zirconium oxide is 1.4 or greater, it is possible to stably change the resistance value of metal-oxide layer 104. In this case, the film thickness of the zirconium oxide may be 1 nm to 5 nm.

In the case of using a tantalum oxide as the metal oxide included in metal-oxide layer 104, when x in Ta Ox representing the composition of the tantalum oxide is 2.1 or greater, it is possible to stably change the resistance value of metal-oxide layer 104.

The composition of each of the above metal oxide layers can be measured using Rutherford backscattering spectrometry.

The material of first electrode 103 and second electrode 106 may be selected from among, for example, platinum, iridium (Ir), palladium (Pd), silver (Ag), nickel, tungsten, copper (Cu), aluminum, tantalum, titanium, titanium nitride (TiN), tantalum nitride (TaN), titanium aluminum nitride (TiAlN), etc.

Specifically, second electrode 106 includes a material, such as platinum, iridium, palladium, or an alloy including at least one of these, which has a catalytic action in which hydrogen atoms are dissociated from gas molecules with hydrogen atoms. First electrode 103 may include a material, such as tungsten, nickel, tantalum, titanium, aluminum, tantalum nitride, and titanium nitride, which has a lower standard electrode potential than a metal included in a metal oxide. The higher the value of the standard electrode potential gets, the less easily a metal oxidizes.

For example, a silicon monocrystalline substrate or a semiconductor substrate can be used for substrate 101, but the present disclosure is not limited to these examples. Since it is possible to form metal-oxide layer 104 at a relatively low substrate temperature, metal-oxide layer 104 can be formed also on, for example, a resin material.

Gas sensor 100 may also include, for example, a fixed resistance, a transistor, or a diode as a load element electrically connected to metal-oxide layer 104.

The resistance change characteristics of gas sensor 100 which exhibit due to voltage application will be described based on the result of actual measurement using a sample device. Note that the resistance change characteristics of gas sensor 100 which exhibit due to hydrogen-containing gas will be described later.

Figure 2:
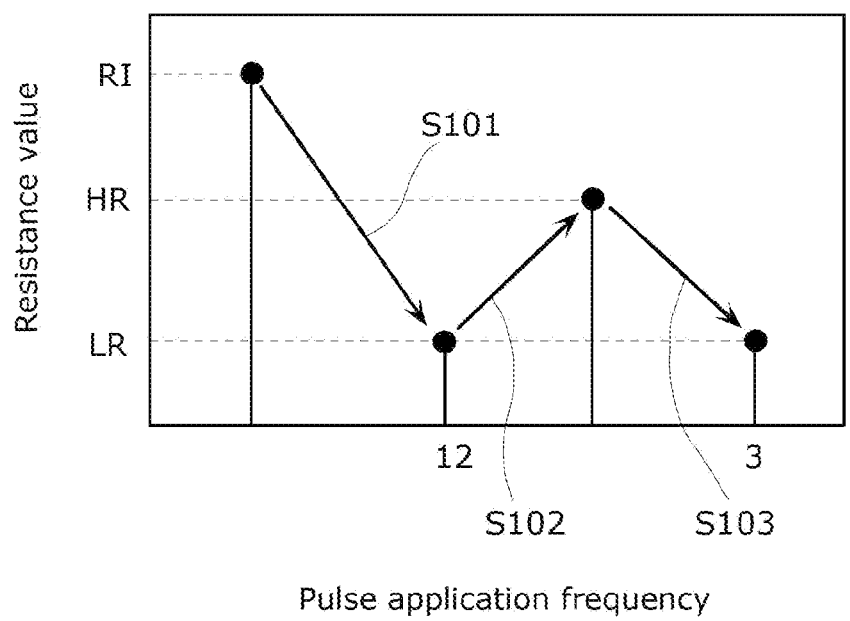
FIG. 2 is a diagram illustrating an example of a state transition of the gas sensor according to the embodiment.

FIG. 2 is a graph showing resistance change characteristics actually measured using a sample device.

In gas sensor 100 that is the sample device with which the measurement result in FIG. 2 is obtained, the size of first electrode 103, second electrode 106, and metal-oxide layer 104 is defined as 0.5 μm×0.5 μm (area: 0.25 μm$^2$). When the composition of a tantalum oxide as metal-oxide layer 104 is represented as $TaO_y$, y=2.47. Moreover, the thickness of metal-oxide layer 104 is defined as 5 nm. When a read voltage (e.g., 0.4 V) is applied across first electrode 103 and second electrode 106 in such gas sensor 100, initial resistance value RI is approximately $10^7 \Omega$ to $10^8 \Omega$.

As illustrated in FIG. 2, when the resistance value of gas sensor 100 is initial resistance value RI (a value higher than resistance value HR in a high-resistance state), the application of an initial break voltage across first electrode 103 and second electrode 106 changes the resistance value to low resistance value LR (S101). Subsequently, when two kinds of voltage pulses, i.e., a positive voltage and a negative voltage, each having a pulse width of 100 ns and a different polarity, are alternately applied across first electrode 103 and second electrode 106 in gas sensor 100 as write voltages, the resistance value across first electrode 103 and second electrode 106 changes as illustrated in FIG. 2.

In other words, when a positive voltage pulse (pulse width: 100 ns) is applied across first electrode 103 and second electrode 106 as a write voltage, the resistance value between the electrodes increases from low resistance value LR to high resistance value HR (S102). When a negative voltage pulse (pulse width: 100 ns) is applied across first electrode 103 and second electrode 106 as a write voltage, on the other hand, the resistance value across the electrodes decreases from high resistance value HR to low resistance value LR (S103). Note that the polarity of a voltage pulse is "positive" when the potential of second electrode 106 is higher than the potential of first electrode 103 serving as a reference, and is "negative" when the potential of second electrode 106 is lower than the potential of first electrode 103 serving as a reference.

Figure 3:
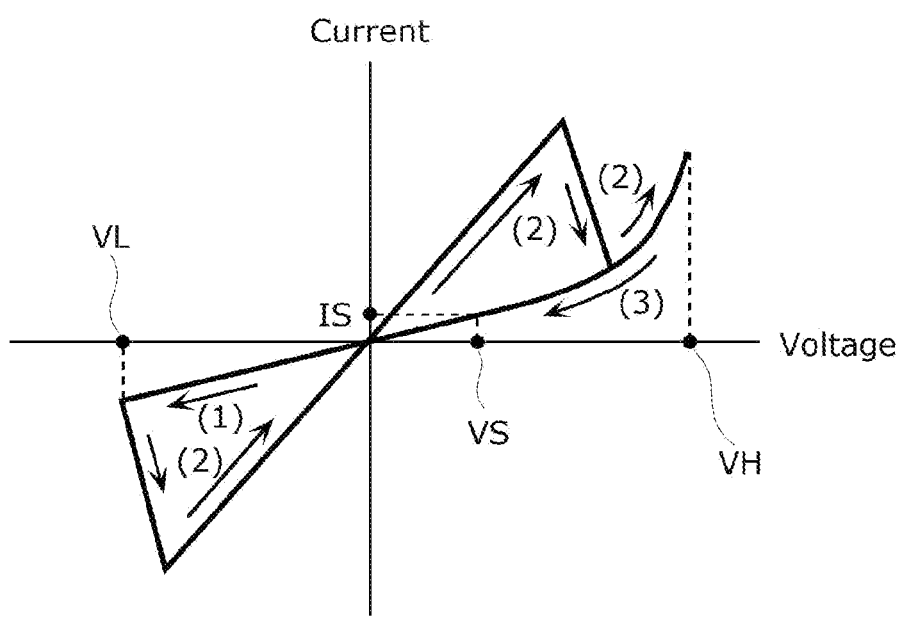
FIG. 3 is a diagram illustrating an example of the current-voltage characteristics of the gas sensor according to the embodiment.

FIG. 3 is a diagram illustrating an example of the current-voltage characteristics of gas sensor 100. FIG. 3 illustrates current-voltage characteristics obtained by measuring a current flowing through gas sensor 100, while applying a fluctuating voltage across first electrode 103 and second electrode 106 in gas sensor 100. Specifically, gas sensor 100 was set to a high-resistance state in advance, and then the applied voltage was changed: (1) firstly from 0 to negative write voltage VL; (2) subsequently from negative write voltage VL to positive write voltage VH; and (3) lastly from positive write voltage VH to 0. The definitions of "positive" and "negative" of a voltage are as described above.

When the applied voltage reaches a negative voltage having a predetermined magnitude, the resistance value across first electrode 103 and second electrode 106 decreases from high resistance value HR to low resistance value LR (the absolute value of the current increases). When the applied voltage reaches a positive voltage having a predetermined magnitude, on the other hand, the resistance value across first electrode 103 and second electrode 106 increases from low resistance value LR to high resistance value HR (the absolute value of the current decreases).

Note that in the application of the present disclosure to gas detection, the resistance value across first electrode 103 and second electrode 106 is measured in accordance with detection current IS that flows when read voltage VS is applied across the electrodes.

[Manufacturing Method and Operation of Gas Sensor]

Next, an example of a method for manufacturing gas sensor 100 will be described with reference to FIG. 4A through FIG. 4G.

Figure 4A:
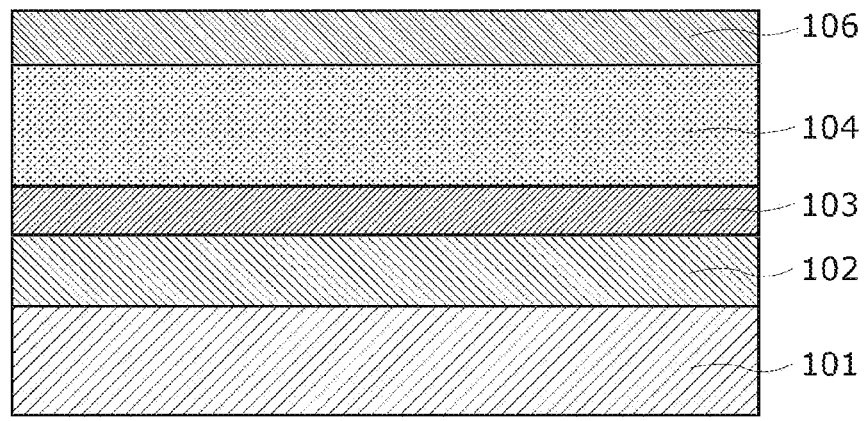
FIG. 4A is a cross-sectional view illustrating an example of a method for manufacturing the gas sensor according to the embodiment.

First, as illustrated in FIG. 4A, insulating film 102 having the thickness of 200 nm is formed, using a thermal oxidation method, on substrate 101 that is made of, for example, monocrystalline silicon. First electrode 103, e.g., a platinum thin film having the thickness of 100 nm, is then formed on insulating film 102 by a sputtering method. Note that an adhesion layer made of, for example, titanium or titanium nitride can be additionally formed between first electrode 103 and insulating film 102 by a sputtering method. Subsequently, an oxygen-deficient metal-oxide layer which becomes metal-oxide layer 104 is formed on first electrode 103 by a reactive sputtering method using, for example, tantalum as a target. Metal-oxide layer 104 is thus formed.

If metal-oxide layer 104 is too thick, a problem is that an initial resistance value becomes too high, or the like, whereas if metal-oxide layer 104 is too thin, a problem is that a stable resistance change cannot be obtained. For the reasons stated above, the thickness of metal-oxide layer 104 may be approximately at least 1 nm and at most 8 nm.

Next, second electrode 106, e.g., a platinum thin film having the thickness of 150 nm, is formed on metal-oxide layer 104 by a sputtering method.

Figure 4B:
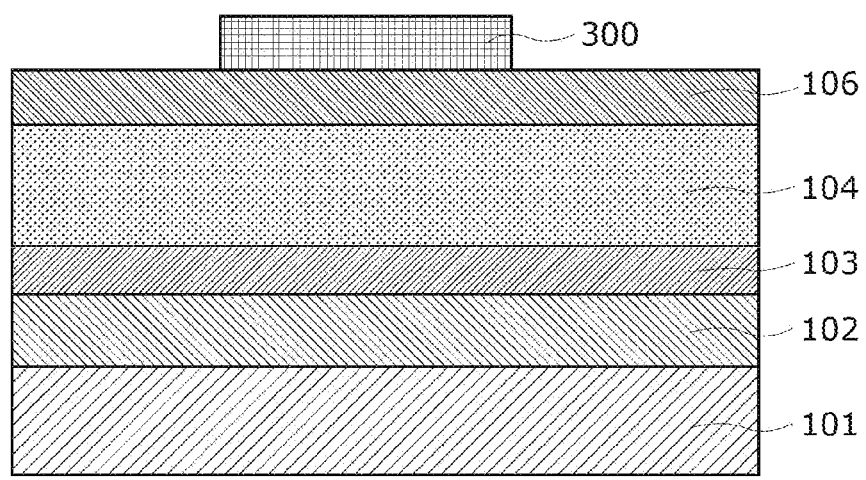
FIG. 4B is a cross-sectional view illustrating the example of the method for manufacturing the gas sensor according to the embodiment.
Figure 4C:
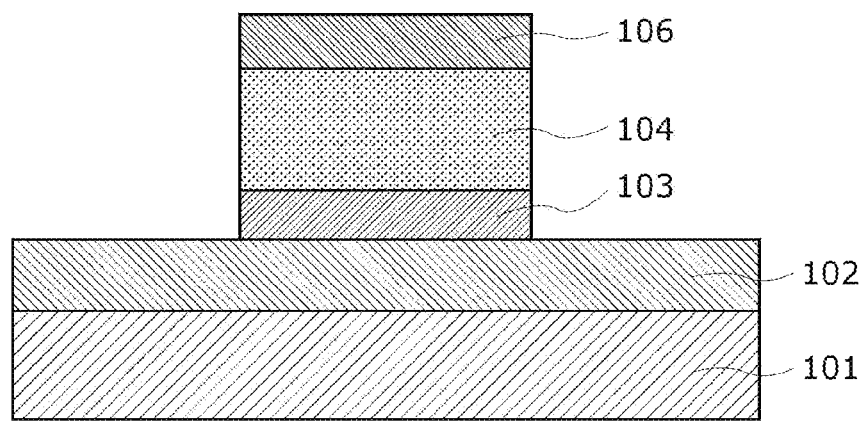
FIG. 4C is a cross-sectional view illustrating the example of the method for manufacturing the gas sensor according to the embodiment.

Next, mask 300 is formed by photoresist masking in a photolithography process, as illustrated in FIG. 4B. After that, first electrode 103, metal-oxide layer 104, and second electrode 106 are formed into the shape of a device by dry etching using mask 300, as illustrated in FIG. 4C.

Figure 4D:
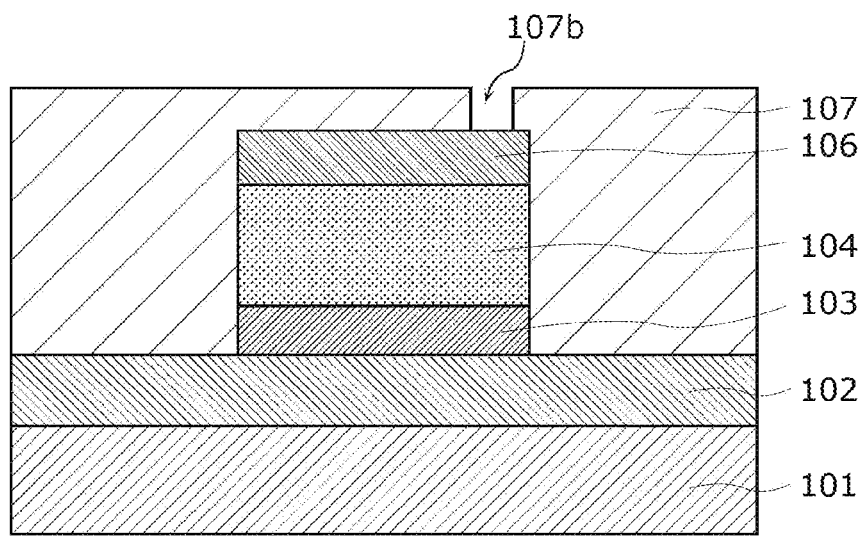
FIG. 4D is a cross-sectional view illustrating the example of the method for manufacturing the gas sensor according to the embodiment.

Subsequently, insulating film 107 is formed to cover insulating film 102, first electrode 103, metal-oxide layer 104, and second electrode 106, as illustrated in FIG. 4D. Insulating film 107 is then provided, through etching, with via hole 107b reaching a part of the upper surface of second electrode 106.

Figure 4E:
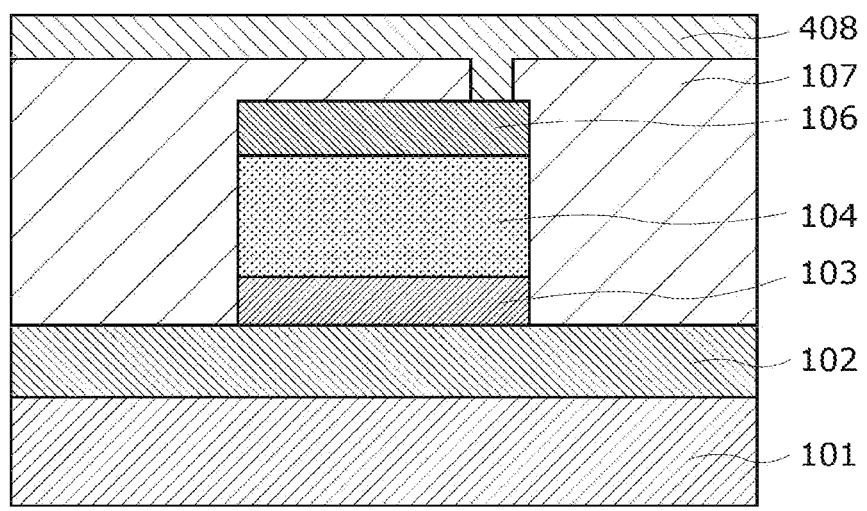
FIG. 4E is a cross-sectional view illustrating the example of the method for manufacturing the gas sensor according to the embodiment.
Figure 4F:
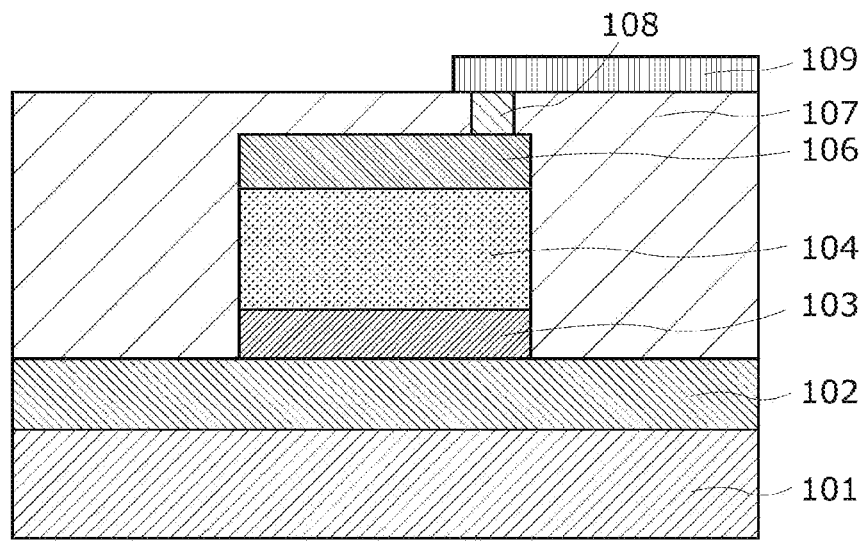
FIG. 4F is a cross-sectional view illustrating the example of the method for manufacturing the gas sensor according to the embodiment.

Next, conductive film 408 is formed to cover the upper surface of insulating film 107 and fill the inside of via hole 107b, as illustrated in FIG. 4E. Subsequently, conductive film 408 on insulating film 107 is removed by chemical mechanical polishing (CMP) to form via 108 in via hole 107b, as illustrated in FIG. 4F. Another conductive film is additionally disposed on insulating film 107 and is then patterned, to form wiring 109 to be connected to via 108.

Figure 4G:
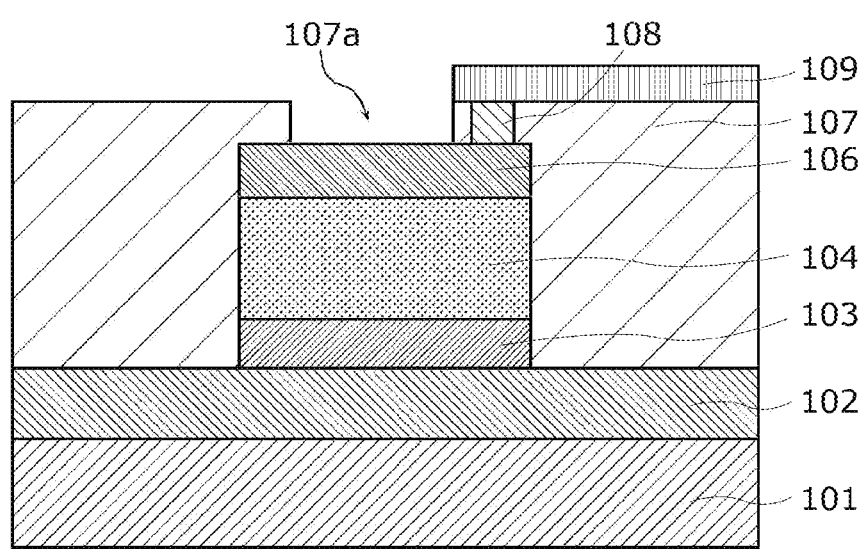
FIG. 4G is a cross-sectional view illustrating the example of the method for manufacturing the gas sensor according to the embodiment.

Next, insulating film 107 is provided, through etching, with aperture 107a that exposes a part of the upper surface of second electrode 106, as illustrated in FIG. 4G.

Subsequently, an initial break voltage is applied across first electrode 103 and second electrode 106 to form local region 105 illustrated in FIG. 1A in metal-oxide layer 104. Gas sensor 100 is thus completed.

[Variation of Gas Sensor]

Figure 5:
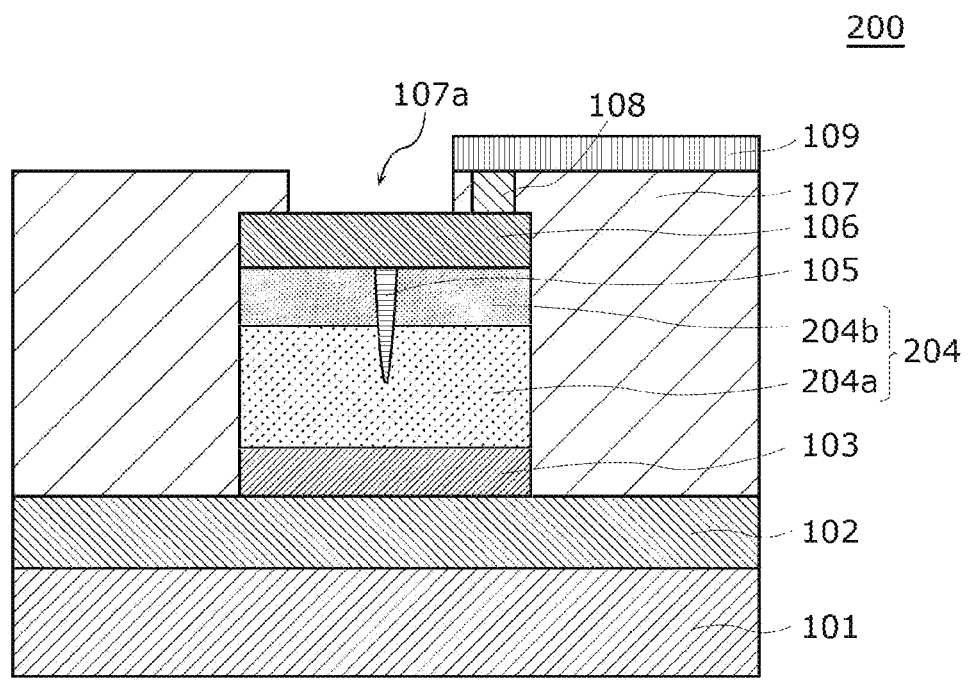
FIG. 5 is a cross-sectional view illustrating an example of a structure of a gas sensor according to a variation.

FIG. 5 is a cross-sectional view illustrating an example of a configuration of a gas sensor according to a variation of the embodiment. The following describes the gas sensor according to the variation, focusing on the difference from gas sensor 100 according to the embodiment.

Gas sensor 200 according to the present variation is different from gas sensor 100 according to the embodiment in that metal-oxide layer 204 is formed by stacking two layers of first metal-oxide layer 204a that is in contact with first electrode 103 and second metal-oxide layer 204b that is in contact with second electrode 106. Note that the number of layers stacked to form metal-oxide layer 204 is not limited to two, and three or more metal-oxide layers may be stacked.

First metal-oxide layer 204a and second metal-oxide layer 204b include local region 105 in which an oxygen deficiency degree reversibly changes in accordance with hydrogen-containing gas and the application of an electric pulse. Local region 105 is formed penetrating through at least second metal-oxide layer 204b to be in contact with second electrode 106.

Stated differently, metal-oxide layer 204 has a layered structure composed of first metal-oxide layer 204a including a first metal oxide and second metal-oxide layer 204b including a second metal oxide. First metal-oxide layer 204a is disposed between first electrode 103 and second metal-oxide layer 204b, and second metal-oxide layer 204b is disposed between first metal-oxide layer 204a and second electrode 106.

The thickness of second metal-oxide layer 204b may be less than that of first metal-oxide layer 204a. In this case, a structure in which local region 105 is not in contact with first electrode 103 can be readily formed. The oxygen deficiency degree of second metal-oxide layer 204b may be lower than that of first metal-oxide layer 204a. In such a case, since the resistance value of second metal-oxide layer 204b is higher than that of first metal-oxide layer 204a, much of the voltage applied to metal-oxide layer 204 is applied to second metal-oxide layer 204b. This structure is useful, for example, for applying an initial break voltage intensively to second metal-oxide layer 204b to decrease an initial break voltage necessary for forming local region 105.

In the present disclosure, when a metal included in first metal-oxide layer 204a and a metal included in second metal-oxide layer 204b are same, the term "oxygen content" may be used instead of "oxygen deficiency degree". The expression "oxygen content is high" corresponds to "oxygen deficiency degree is low" and the expression "oxygen content is low" corresponds to "oxygen deficiency degree is high".

However, as will be described later, metal-oxide layer 204 according to this embodiment is not limited to the case where the metal included in first metal-oxide layer 204a and the metal included in second metal-oxide layer 204b are same, and the metals may be different from each other. In other words, first metal-oxide layer 204a and second metal-oxide layer 204b may be oxides of different metals.

When the first metal included in first metal-oxide layer 204a and the second metal included in second metal-oxide layer 204b are same, an oxygen content has a corresponding relationship with an oxygen deficiency degree. In other words, when the oxygen content of second metal oxide 204b is higher than that of first metal oxide 204a, the oxygen deficiency degree of second metal oxide 204b is lower than that of first metal oxide 204a.

Metal-oxide layer 204 includes local region 105 in the vicinity of the interface between first metal-oxide layer 204a and second metal-oxide layer 204b. Local region 105 has an oxygen deficiency degree that is higher than that of second metal-oxide layer 204b and is different from that of first metal-oxide layer 204a.

Local region 105 is formed in metal-oxide layer 204 by the application of an initial break voltage across first electrode 103 and second electrode 106. With the initial break voltage being applied, local region 105, which is in contact with second electrode 106, penetrates through second metal-oxide layer 204b to partially penetrate into first metal-oxide layer 204a, and is not in contact with first electrode 103, is formed.

Gas Sensor Driving Method According to Reference Example

A basic resistance change phenomenon that occurs due to hydrogen-containing gas in a gas sensor configured as described above will be described based on a gas sensor driving method according to a reference example. Although the following describes a gas sensor driving method using gas sensor 200, the same description also applies to gas sensor 100.

Figure 6:
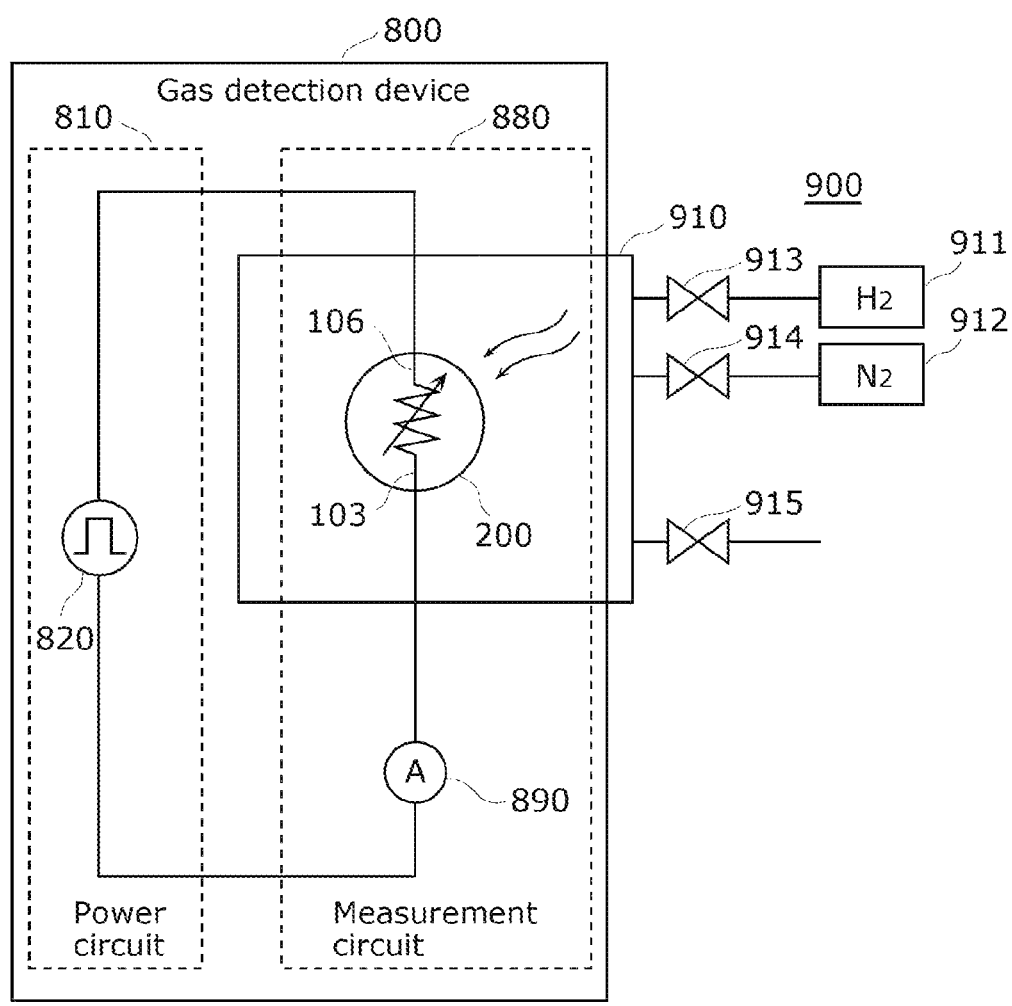
FIG. 6 is a functional block diagram illustrating an example of a configuration of a gas detection device according to a reference example.

FIG. 6 is a functional block diagram illustrating an example of a configuration of a gas detection device for implementing the gas sensor driving method according to the reference example. As illustrated in FIG. 6, gas detection device 800 includes power circuit 810 and measurement circuit 880. Power circuit 810 includes voltage pulse generator circuit 820, and measurement circuit 880 includes gas sensor 200 and current measurement circuit 890. Voltage pulse generator circuit 820 repeatedly generates a positive voltage pulse.

FIG. 6 also illustrates gas supply system 900. In gas supply system 900, closed container 910 is connected to hydrogen tank 911 and nitrogen tank 912 respectively via intake valves 913 and 914, and gas inside closed container 910 can be evacuated via exhaust valve 915. Gas sensor 200 in gas detection device 800 is stored in closed container 910.

Figure 7A:
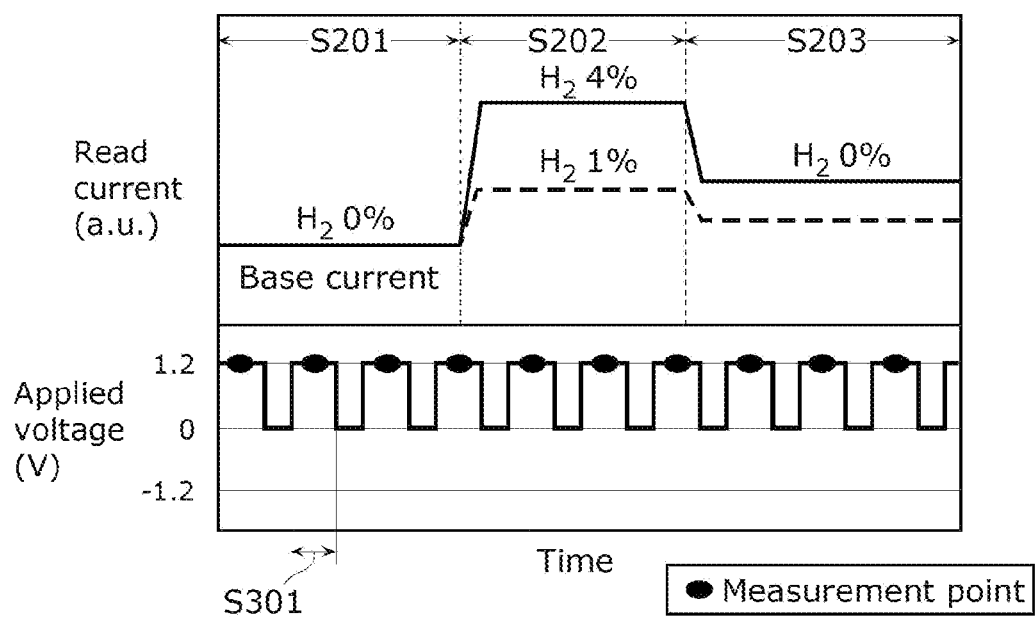
FIG. 7A is a diagram illustrating an example of a method for driving a gas sensor according to the reference example.

FIG. 7A is a diagram illustrating an example of a method for driving gas sensor 200 according to the reference example. In FIG. 7A, an applied voltage indicates the time waveform of a voltage applied across first electrode 103 and second electrode 106 in gas sensor 200. The polarity of the applied voltage is "positive" when the potential of second electrode 106 is higher than the potential of first electrode 103 serving as a reference, and is "negative" when the potential of second electrode 106 is lower than the potential of first electrode 103 serving as a reference. A read current indicates a waveform obtained by joining, along a time axis direction, the value of a current that flows across first electrode 103 and second electrode 106 at each of the measurement points that are set during the application of a positive voltage.

In the driving method according to the reference example, a positive voltage of 1.2 V is repeatedly applied (step S301), as illustrated in FIG. 7A. A single positive voltage pulse is applied in a single application of the positive voltage.

A read current was measured while a voltage is applied in accordance with the driving method according to the reference example. First, gas sensor 200 is placed in nitrogen gas introduced into closed container 910, hydrogen gas is subsequently introduced into closed container 910, and after a certain period of time, the introduced gas is switched from hydrogen gas to nitrogen gas. The hydrogen gas here is a specific example of hydrogen-containing gas.

The read current in FIG. 7A schematically indicates the result of this measurement, and the horizontal axis indicates three periods which are the former nitrogen introduction (step S201), hydrogen introduction (step S202), and the latter nitrogen introduction (step S203). In the hydrogen introduction in step S202, the measurement was conducted under two different conditions, one case where the concentration of hydrogen is 4% and the other case where the concentration of hydrogen is 1%.

During the nitrogen introduction in step S201, a read current indicated a predetermined current value. Hereinafter, a current value is referred to as a base current. In step S202, the read current increased after the introduced gas was switched from nitrogen gas to hydrogen gas, and hydrogen gas was detected. Subsequently, when the introduced gas was switched from hydrogen gas to nitrogen gas in step S203, the read current decreased but did not return to the base current.

Based on the result, the inventors infer, as follows, the mechanism of a resistance change phenomenon that occurs in gas sensor 200 due to the driving method according to the reference example.

Figure 7B:
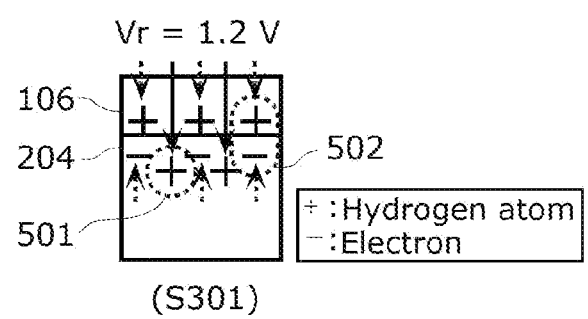
FIG. 7B is a conceptual diagram illustrating an example of a resistance change phenomenon that occurs in the driving method according to the reference example.

FIG. 7B is a conceptual diagram illustrating the resistance change phenomenon that occurs in the driving method according to the reference example. As illustrated in FIG. 7B, with the application of the positive voltage in step S301 performed in step S202, hydrogen atoms 501 derived from hydrogen gas are scattered in metal-oxide layer 204. Moreover, dipoles 502 each including a hydrogen atom and an electron are formed at the interface between second electrode 106 and metal-oxide layer 204.

A level and dipoles 502 that are formed by scattered hydrogen atoms 501 allow an easy flow of the current across first electrode 103 and second electrode 106, and the read current increases (stated differently, the effective resistance value of metal-oxide layer 204 decreases).

With the driving method according to the reference example, which applies only a positive voltage, scattered hydrogen atoms 501 and dipoles 502 still remain even after the concentration of hydrogen has dropped to 0% due to the nitrogen introduction in step S203. It is conceivable that this is why the value of the read current in step S203 did not return to the base current.

Figure 8:
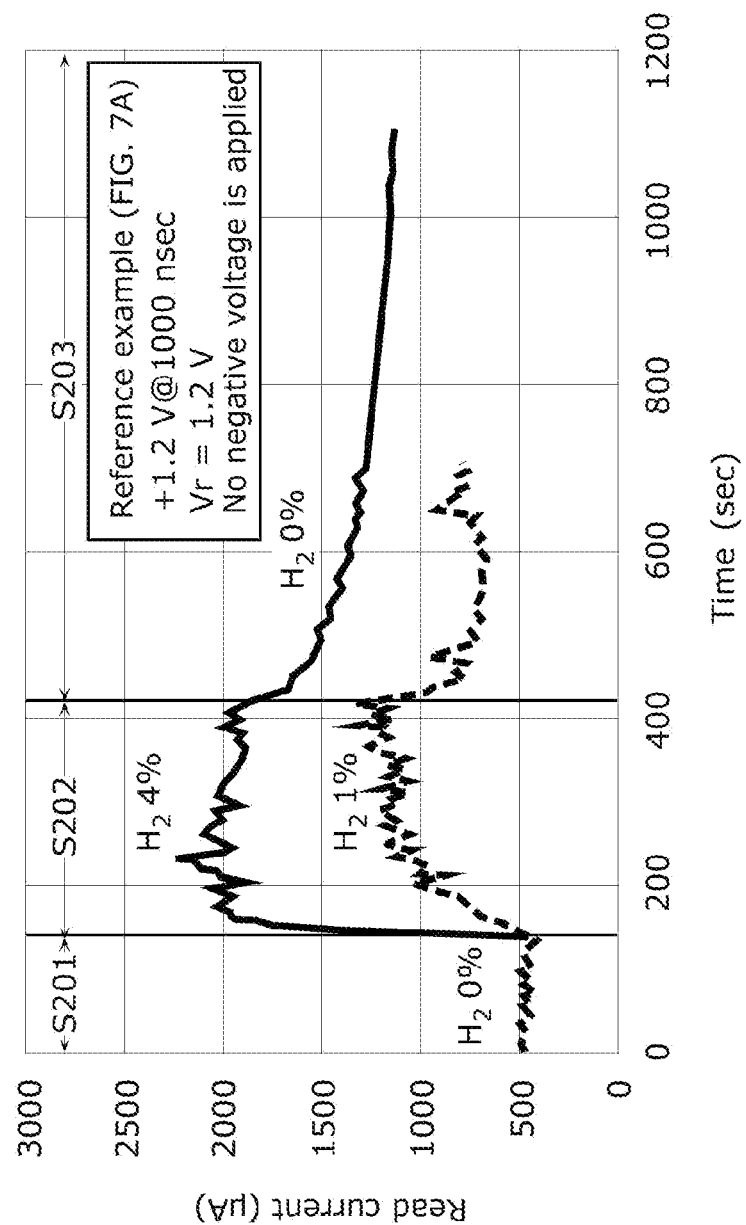
FIG. 8 is a graph illustrating an example of a read current in the reference example.

FIG. 8 is a graph illustrating, in more detail, an example of the result of the actual measurement of a read current according to the reference example. FIG. 8 illustrates the result of the actual measurement of a read current obtained when a positive voltage of 1.2 V for reading is applied after a positive voltage pulse of 1.2 V is applied for 1000 nanoseconds in step S301. The measurement result in FIG. 8 is a specific example of the read current in FIG. 7A. Note that in the reference example, the application of a negative voltage across first electrode 103 and second electrode 106 is not performed, which is different from a driving method according to any one of the embodiments to be described later.

That the read current in step S203 does not return to the base current could be an impediment to the stable detection of hydrogen-containing gas. For example, when the read current in step S203 stays high at a current value of at least a threshold, which corresponds to the case where hydrogen gas with low concentration (e.g., 1%) is detected in step S202, the detection of hydrogen gas with low concentration can be no longer performed.

In view of this, the present disclosure proposes a gas sensor driving method of repeatedly applying a positive voltage and a negative voltage. The following describes the gas sensor driving method according to the present disclosure, using embodiments.

Gas Sensor Driving Method According to Embodiment 1

FIG. 9 is a functional block diagram illustrating an example of a configuration of a gas detection device for implementing a gas sensor driving method according to Embodiment 1. Gas detection device 801 illustrated in FIG. 9 includes power circuit 811 and measurement circuit 880. Power circuit 811 includes voltage pulse generator circuits 820 and 821, and switch circuit 830, whereas measurement circuit 880 includes gas sensor 200 and current measurement circuit 890.

FIG. 9 also illustrates gas supply system 900 which is the same as that described in FIG. 6. Gas sensor 200 in gas detection device 801 is stored in closed container 910 of gas supply system 900. Structural elements that are substantially the same as those previously described are assigned with like reference signs, and description is omitted.

Voltage pulse generator circuit 820 generates a positive voltage pulse, and voltage pulse generator circuit 821 generates a negative voltage pulse. Switch circuit 830 selects one of a positive voltage pulse generated by voltage pulse generator circuit 820 and a negative voltage pulse generated by voltage pulse generator circuit 821. The voltage pulse selected by switch circuit 830 is applied across first electrode 103 and second electrode 106 in gas sensor 200.

Figure 10A:
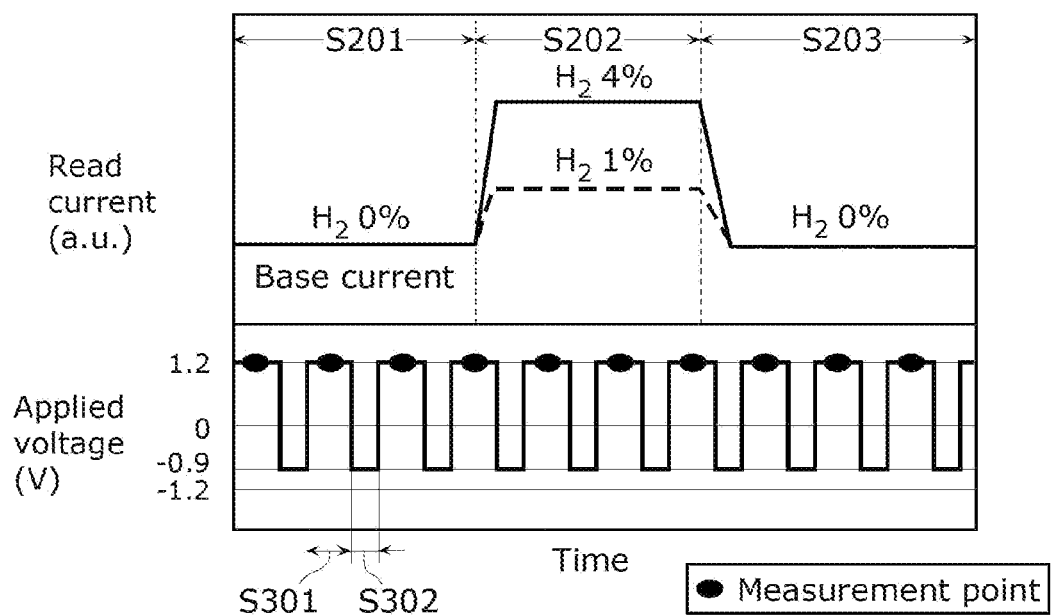
FIG. 10A is a diagram illustrating an example of a method for driving a gas sensor according to Embodiment 1.

FIG. 10A is a diagram illustrating an example of the driving method of gas sensor 200 according to Embodiment 1. FIG. 10A illustrates an applied voltage and a read current across first electrode 103 and second electrode 106 in gas sensor 200, using the same representation method as that used in FIG. 7A.

In the driving method according to Embodiment 1, a positive voltage and a negative voltage are repeatedly applied (steps S301 and S302), as illustrated in FIG. 10A. A single positive voltage pulse is applied in a single application of the positive voltage, and a single negative voltage pulse is applied in a single application of the negative voltage.

Under the same circumstances as in the reference example, a read current was measured while a voltage was applied in accordance with the driving method according to Embodiment 1. The read current in FIG. 10A schematically illustrates the result of the measurement.

During the hydrogen introduction in step S201, the value of the read current indicated a base current. In step S202, the read current increased after the introduced gas was switched from nitrogen gas to hydrogen gas, and hydrogen gas was detected. Subsequently, when the introduced gas was switched from hydrogen gas to nitrogen gas in step S203, the read current decreased to the base current.

Based on the result, the inventors infer, as follows, the mechanism of a resistance change phenomenon that occurs in gas sensor 200 due to the driving method according to Embodiment 1.

Figure 10B:
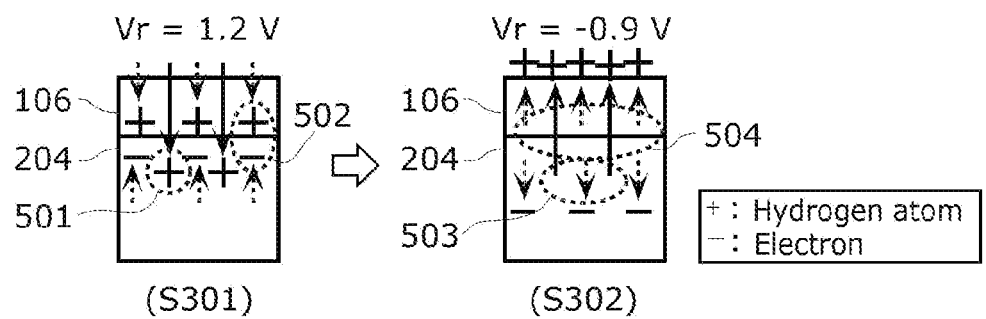
FIG. 10B is a conceptual diagram illustrating an example of a resistance change phenomenon that occurs in the driving method according to Embodiment 1.

FIG. 10B is a conceptual diagram illustrating the resistance change phenomenon that occurs in the driving method according to Embodiment 1. As is the case of the driving method according to the reference example, with the application of the positive voltage (e.g., 1.2 V) in step S301 performed in step S202, hydrogen atoms 501 derived from hydrogen gas are scattered in metal-oxide layer 204. Moreover, dipoles 502 each including a hydrogen atom and an electron are formed at the interface between second electrode 106 and metal-oxide layer 204.

A level and dipoles 502 that are formed by scattered hydrogen atoms 501 allow an easy flow of the current across first electrode 103 and second electrode 106, and the read current increases (stated differently, the effective resistance value of metal-oxide layer 204 decreases).

With the application of the negative voltage (e.g., −0.9 V) in step S302, hydrogen atoms 501 move to second electrode 106 and do not remain in metal-oxide layer 204 (see dotted circle 503). Dipoles 502 also disappear (see dotted circle 504). As a result, the value of the read current returns to the base current.

Figure 11:
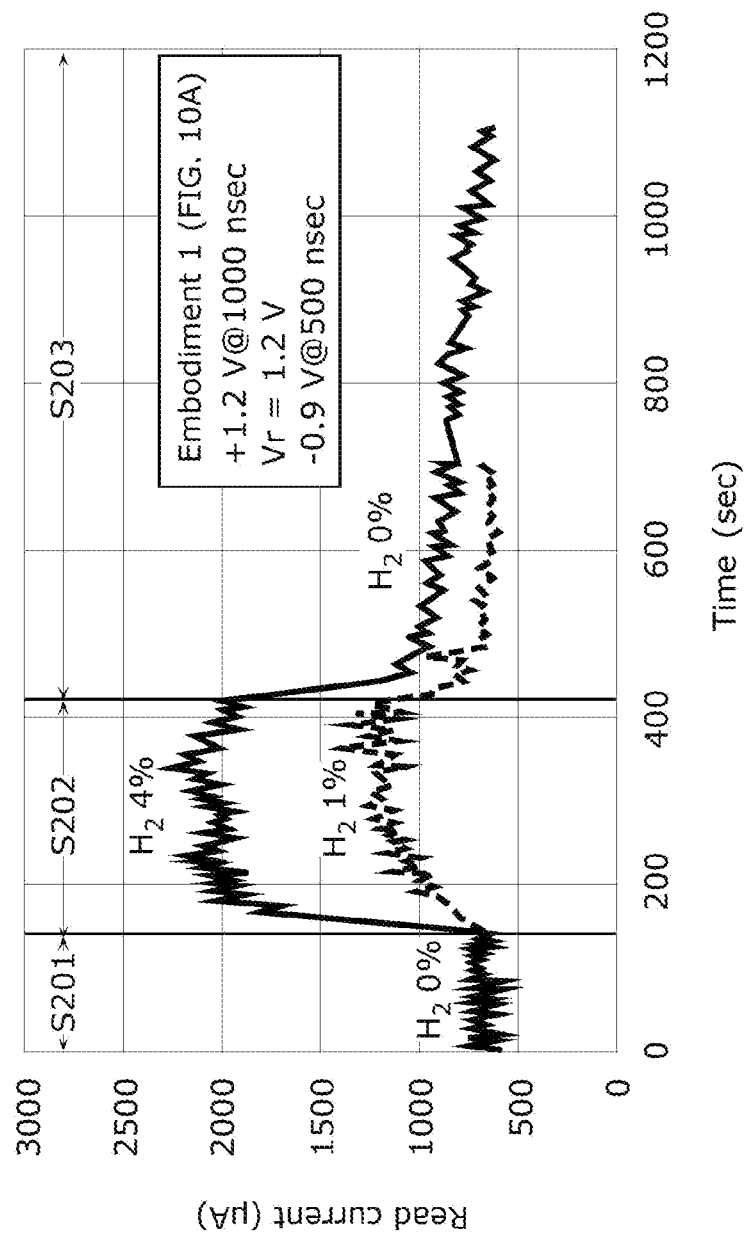
FIG. 11 is a graph illustrating an example of a read current in Embodiment 1.

FIG. 11 is a graph illustrating, in more detail, an example of the result of the actual measurement of a read current according to Embodiment 1. FIG. 11 illustrates the result of the actual measurement of a read current obtained when a positive voltage pulse of 1.2 V is applied for 1000 nanoseconds and a positive voltage of 1.2 V for reading is subsequently applied in step S301, and a negative voltage pulse of −0.9 V is applied for 500 nanoseconds in step S302. The measurement result in FIG. 11 is a specific example of the read current in FIG. 10A.

In the driving method according to Embodiment 1, a positive voltage and a negative voltage are repeatedly applied across first electrode 103 and second electrode 106. Accordingly, it is possible to bring back, to the base current, the value of the read current after the detection of hydrogen-containing gas, to repeat the stable detection of hydrogen-containing gas with a simple procedure that does not require any conditional judgment.

Although the above description has illustrated an example in which a positive voltage and a negative voltage are 1.2 V and −0.9 V, respectively, the present disclosure is not limited to this example. An appropriate voltage such that the absolute value of an applied voltage in the application of the positive voltage is smaller than the absolute value of the aforementioned initial break voltage and is larger than the absolute value of an applied voltage in the application of the negative voltage is used for the positive voltage. Moreover, the waveforms of the positive voltage pulse and the negative voltage pulse are not limited to square waves, and appropriate waveforms are used. Accordingly, the same effects can be obtained since the aforementioned mechanism of the resistance change phenomenon works. In addition, the same effects can be obtained even with gas detection device 801 that implements the driving method according to Embodiment 1.

Gas Sensor Driving Method According to Embodiment 2

Figure 12:
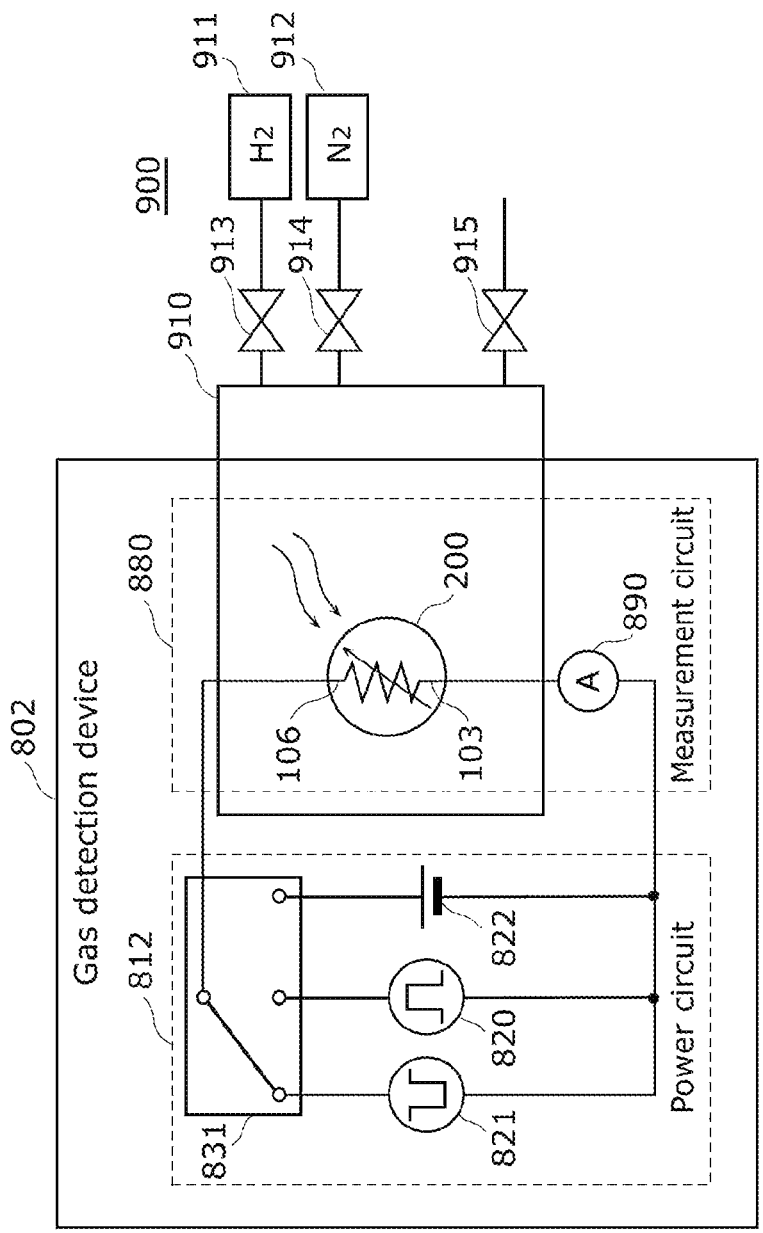
FIG. 12 is a functional block diagram illustrating an example of a configuration of a gas detection device according to Embodiment 2.

FIG. 12 is a functional block diagram illustrating an example of a configuration of a gas detection device for implementing a gas sensor driving method according to Embodiment 2. Gas detection device 802 illustrated in FIG. 12 includes power circuit 812 and measurement circuit 880. Power circuit 812 includes voltage pulse generator circuits 820 and 821, constant voltage generator circuit 822, and switch circuit 831. Measurement circuit 880 includes gas sensor 200 and current measurement circuit 890.

FIG. 12 also illustrates gas supply system 900 which is the same as that described in FIG. 6. Gas sensor 200 in gas detection device 802 is stored in closed container 910 of gas supply system 900. Structural elements that are substantially the same as those previously described are assigned with like reference signs, and description is omitted.

Constant voltage generator circuit 822 generates a positive voltage for reading. Hereinafter, a positive voltage pulse generated by voltage pulse generator circuit 820 is referred to as a first positive voltage, and a positive voltage generated by constant voltage generator circuit 822 is referred to as a second positive voltage.

Switch circuit 831 cyclically selects, in a predetermined order, a positive voltage pulse generated by voltage pulse generator circuit 820, a negative voltage pulse generated by voltage pulse generator circuit 821, and a positive voltage for reading generated by constant voltage generator circuit 822. The voltage pulse selected by switch circuit 831 is applied across first electrode 103 and second electrode 106 in gas sensor 200.

Figure 13A:
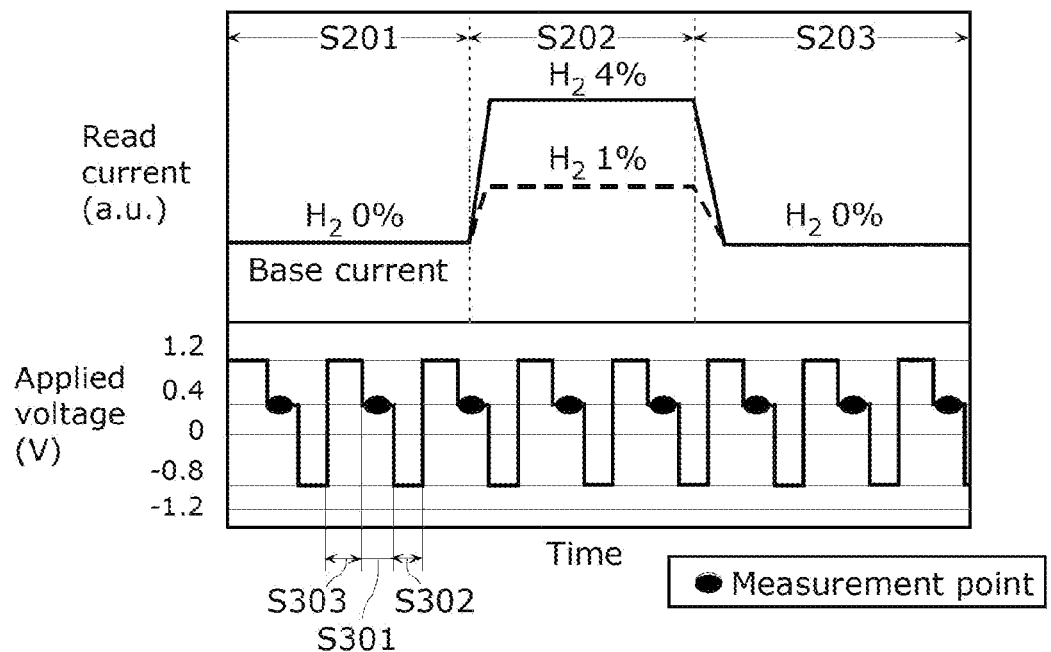
FIG. 13A is a diagram illustrating an example of a method for driving a gas sensor according to Embodiment 2.

FIG. 13A is a diagram illustrating an example of the driving method of gas sensor 200 according to Embodiment 2. FIG. 13A illustrates an applied voltage and a read current across first electrode 103 and second electrode 106 in gas sensor 200, using the same representation method as that used in FIG. 7A.

In the driving method according to Embodiment 2, a first positive voltage, a second positive voltage, and a negative voltage are repeatedly applied in this order (steps S303, S301, and S302), as illustrated in FIG. 13A. A single positive voltage pulse is applied in a single application of the first positive voltage, and a single negative voltage pulse is applied in a single application of the negative voltage.

Under the same circumstances as in the reference example, a read current was measured while a voltage was applied in accordance with the driving method according to Embodiment 2. The read current in FIG. 13A schematically illustrates the result of the measurement.

During the hydrogen introduction in step S201, the value of the read current indicated a base current. In step S202, the read current increased after the introduced gas was switched from nitrogen gas to hydrogen gas, and hydrogen gas was detected. Subsequently, when the introduced gas was switched from hydrogen gas to nitrogen gas in step S203, the read current decreased to the base current.

Based on the result, the inventors infer, as follows, the mechanism of a resistance change phenomenon that occurs in gas sensor 200 due to the driving method according to Embodiment 2.

Figure 13B:
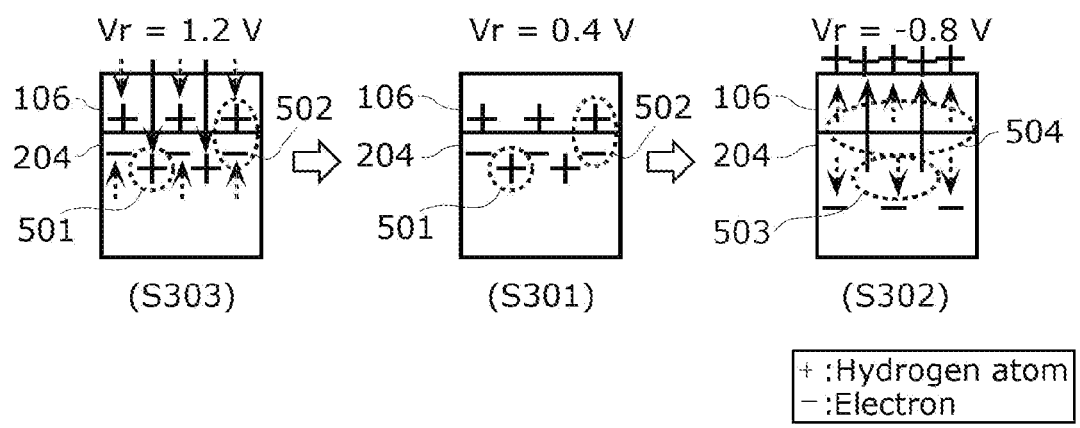
FIG. 13B is a conceptual diagram illustrating an example of a resistance change phenomenon that occurs in the driving method according to Embodiment 2.

FIG. 13B is a conceptual diagram illustrating the resistance change phenomenon that occurs in the driving method according to Embodiment 2. As is the case of the driving method according to the reference example, with the application of the first positive voltage (e.g., 1.2 V) in step S303 performed in step S202, hydrogen atoms 501 derived from hydrogen gas are scattered in metal-oxide layer 204. Moreover, dipoles 502 each including a hydrogen atom and an electron are formed at the interface between second electrode 106 and metal-oxide layer 204.

A level and dipoles 502 that are formed by scattered hydrogen atoms 501 allow an easy flow of the current across first electrode 103 and second electrode 106, and the read current increases (stated differently, the effective resistance value of metal-oxide layer 204 decreases).

In step S301, the application of the second positive voltage (e.g., 0.4 V) maintains hydrogen atoms 501 and dipoles 502, thereby keeping a state in which the current easily flows.

With the application of the negative voltage (e.g., −0.8 V) in step S302, hydrogen atoms 501 move to second electrode 106 and do not remain in metal-oxide layer 204 (see dotted circle 503). Dipoles 502 also disappear (see dotted circle 504). As a result, the value of the read current returns to the base current.

Figure 14:
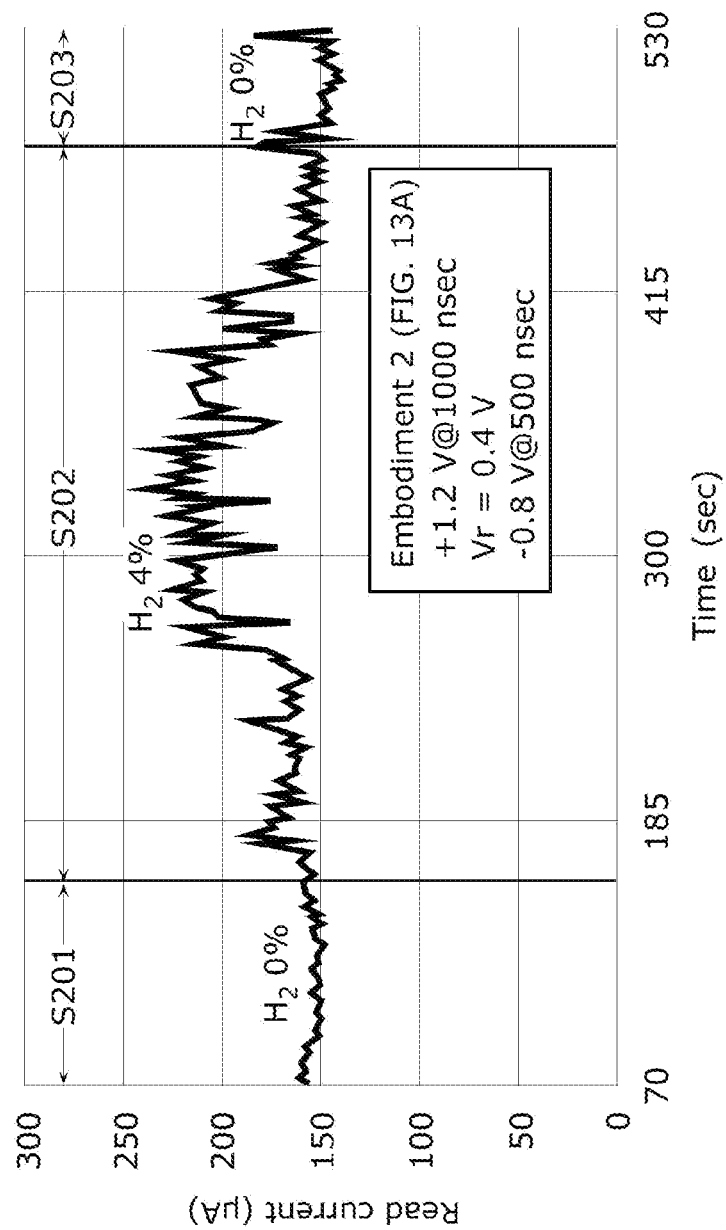
FIG. 14 is a graph illustrating an example of a read current in Embodiment 2.

FIG. 14 is a graph illustrating, in more detail, an example of the result of the actual measurement of a read current according to Embodiment 2. FIG. 14 illustrates the result of the actual measurement of a read current obtained when a positive voltage pulse of 1.2 V is applied for 1000 nanoseconds and a positive voltage of 0.4 V for reading is subsequently applied in step S301, and a negative voltage pulse of −0.8 V is applied for 500 nanoseconds in step S302. The measurement result in FIG. 14 is a specific example of the read current in FIG. 13A.

In the driving method according to Embodiment 2, a first positive voltage, a second positive voltage, and a negative voltage are repeatedly applied in this order across first electrode 103 and second electrode 106. Accordingly, it is possible to bring back, to the base current, the value of the read current after the detection of hydrogen-containing gas, to repeat the stable detection of hydrogen-containing gas with a simple procedure that does not require any conditional judgment. Moreover, since a read current is measured using the second positive voltage lower than the first positive voltage, it is possible to operate with less power consumption compared with the driving method according to Embodiment 1.

Although the above description has illustrated an example in which a first positive voltage, a second positive voltage, and a negative voltage are 1.2 V, 0.4 V, and −0.8 V, respectively, the present disclosure is not limited to this example. An appropriate voltage such that the absolute value of an applied voltage in the application of the first positive voltage is smaller than the absolute value of the aforementioned initial break voltage and is larger than the absolute value of an applied voltage in the application of the negative voltage is used for the first positive voltage. An appropriate voltage such that the absolute value of an applied voltage in the application of the second positive voltage is smaller than the absolute value of an applied voltage in the application of the first positive voltage is used for the second positive voltage. Moreover, the waveforms of the first positive voltage and the negative voltage are not limited to square waves, and appropriate waveforms are used. Accordingly, the same effects can be obtained since the aforementioned mechanism of the resistance change phenomenon works. In addition, the same effects can be obtained even with gas detection device 802 that implements the driving method according to Embodiment 2.

Gas Sensor Driving Method According to Embodiment 3

A method for driving gas sensor 200 according to Embodiment 3 is implemented by gas detection device 802 illustrated in FIG. 12.

Figure 15A:
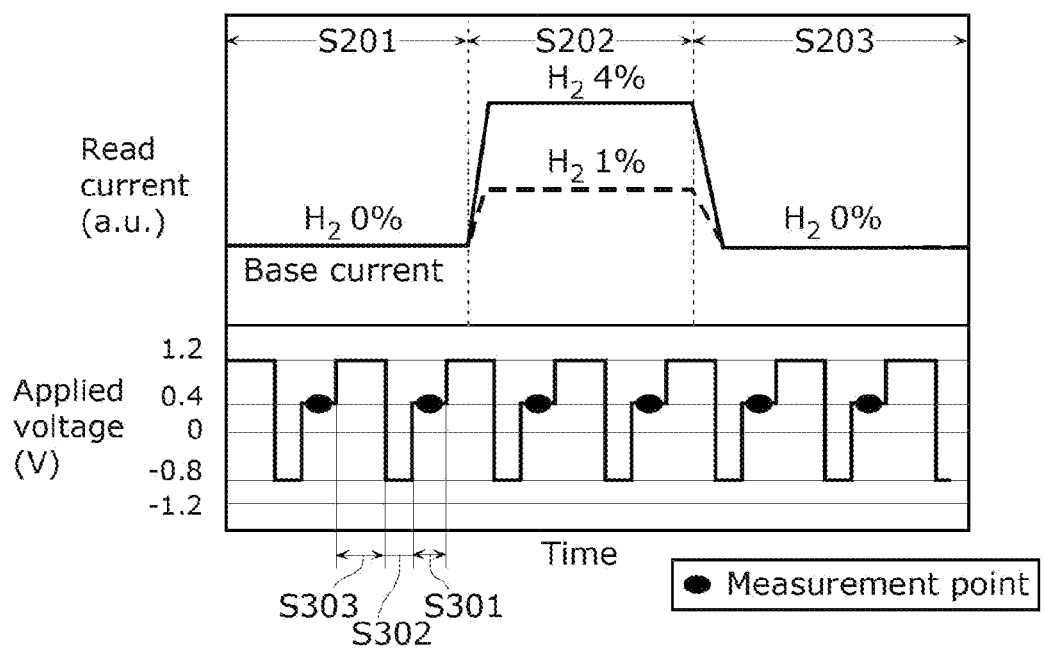
FIG. 15A is a diagram illustrating an example of a method for driving a gas sensor according to Embodiment 3.

FIG. 15A is a diagram illustrating an example of the driving method of gas sensor 200 according to Embodiment 3. FIG. 15A illustrates an applied voltage and a read current across first electrode 103 and second electrode 106 in gas sensor 200, using the same representation method as that used in FIG. 7A.

In the driving method according to Embodiment 3, a first positive voltage, a negative voltage, and a second positive voltage are repeatedly applied in this order (steps S303, S302, and S301), as illustrated in FIG. 15A. A single positive voltage pulse is applied in a single application of the first positive voltage, and a single negative voltage pulse is applied in a single application of the negative voltage.

Under the same circumstances as in the reference example, a read current was measured while a voltage was applied in accordance with the driving method according to Embodiment 3. The read current in FIG. 15A schematically illustrates the result of the measurement.

During the hydrogen introduction in step S201, the value of the read current indicated a base current. In step S202, the read current increased after the introduced gas was switched from nitrogen gas to hydrogen gas, and hydrogen gas was detected. Subsequently, when the introduced gas was switched from hydrogen gas to nitrogen gas in step S203, the read current decreased to the base current.

Based on the result, the inventors infer, as follows, the mechanism of a resistance change phenomenon that occurs in gas sensor 200 due to the driving method according to Embodiment 3.

Figure 15B:
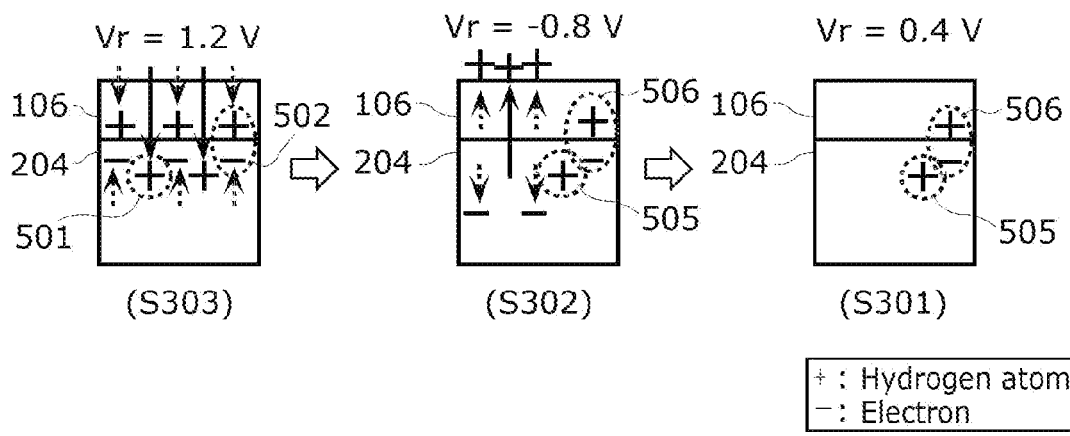
FIG. 15B is a conceptual diagram illustrating an example of a resistance change phenomenon that occurs in the driving method according to Embodiment 3.

FIG. 15B is a conceptual diagram illustrating the resistance change phenomenon that occurs in the driving method according to Embodiment 3. As is the case of the driving method according to the reference example, with the application of the first positive voltage (e.g., 1.2 V) in step S303 performed in step S202, hydrogen atoms 501 derived from hydrogen gas are scattered in metal-oxide layer 204. Moreover, dipoles 502 each including a hydrogen atom and an electron are formed at the interface between second electrode 106 and metal-oxide layer 204.

A level and dipoles 502 that are formed by scattered hydrogen atoms 501 allow an easy flow of the current across first electrode 103 and second electrode 106, and the read current increases (stated differently, the effective resistance value of metal-oxide layer 204 decreases).

With the application of the negative voltage (e.g., −0.8 V) in step S302, hydrogen atoms move to second electrode 106, but part of hydrogen atoms 505 remain in metal-oxide layer 204. Part of dipoles 506 also remain. Due to the remaining hydrogen atoms 501 and dipoles 506, the current flows more easily compared to the state before the detection of hydrogen-containing gas.

In step S301, the second positive voltage (e.g., 0.4 V) is applied, and with the read current, which corresponds to the remaining hydrogen atoms 505 and dipoles 506, flowing, hydrogen-containing gas is detected.

Figure 16:
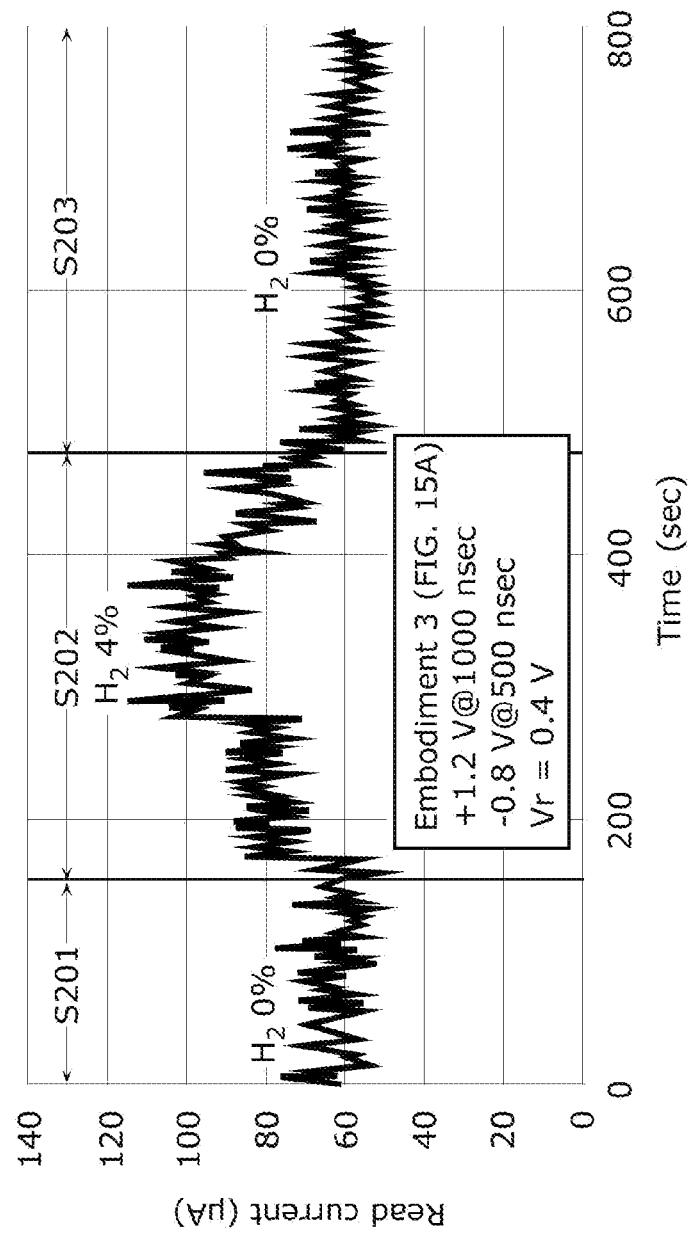
FIG. 16 is a graph illustrating an example of a read current in Embodiment 3.

FIG. 16 is a graph illustrating, in more detail, an example of the result of the actual measurement of a read current according to Embodiment 3. FIG. 16 illustrates the result of the actual measurement of a read current obtained when a positive voltage pulse of 1.2 V is applied for 1000 nanoseconds in step S303, a negative voltage pulse of −0.8 V is subsequently applied for 500 nanoseconds in step S302, and a positive voltage of 0.4 V for reading is applied in step S301. The measurement result in FIG. 16 is a specific example of the read current in FIG. 15A. The measurement result in FIG. 16 shows that the value of the read current in step S203 returns to the base current.

In the driving method according to Embodiment 3, a first positive voltage, a negative voltage, and a second positive voltage are repeatedly applied in this order across first electrode 103 and second electrode 106. Accordingly, it is possible to bring back, to the base current, the value of the read current after the detection of hydrogen-containing gas, to repeat the stable detection of hydrogen-containing gas with a simple procedure that does not require any conditional judgment. Moreover, since a read current is measured using the second positive voltage lower than the first positive voltage, it is possible to operate with less power consumption compared with the driving method according to Embodiment 1.

Although the above description has illustrated an example in which a first positive voltage, a negative voltage, and a second positive voltage are 1.2 V, −0.8 V, and 0.4 V, respectively, the present disclosure is not limited to this example. An appropriate voltage such that the absolute value of an applied voltage in the application of the first positive voltage is smaller than the absolute value of the aforementioned initial break voltage and is larger than the absolute value of an applied voltage in the application of the negative voltage is used for the first positive voltage. An appropriate voltage such that the absolute value of an applied voltage in the application of the second positive voltage is smaller than the absolute value of an applied voltage in the application of the first positive voltage is used for the second positive voltage.

Moreover, the waveforms of the first positive voltage and the negative voltage are not limited to square waves, and appropriate waveforms are used. Accordingly, the same effects can be obtained since the aforementioned mechanism of the resistance change phenomenon works. In addition, the same effects can be obtained even with gas detection device 802 that implements the driving method according to Embodiment 3.

Gas Sensor Driving Method According to Embodiment 4

A method for driving gas sensor 200 according to Embodiment 4 is implemented by gas detection device 802 illustrated in FIG. 12.

Figure 17:
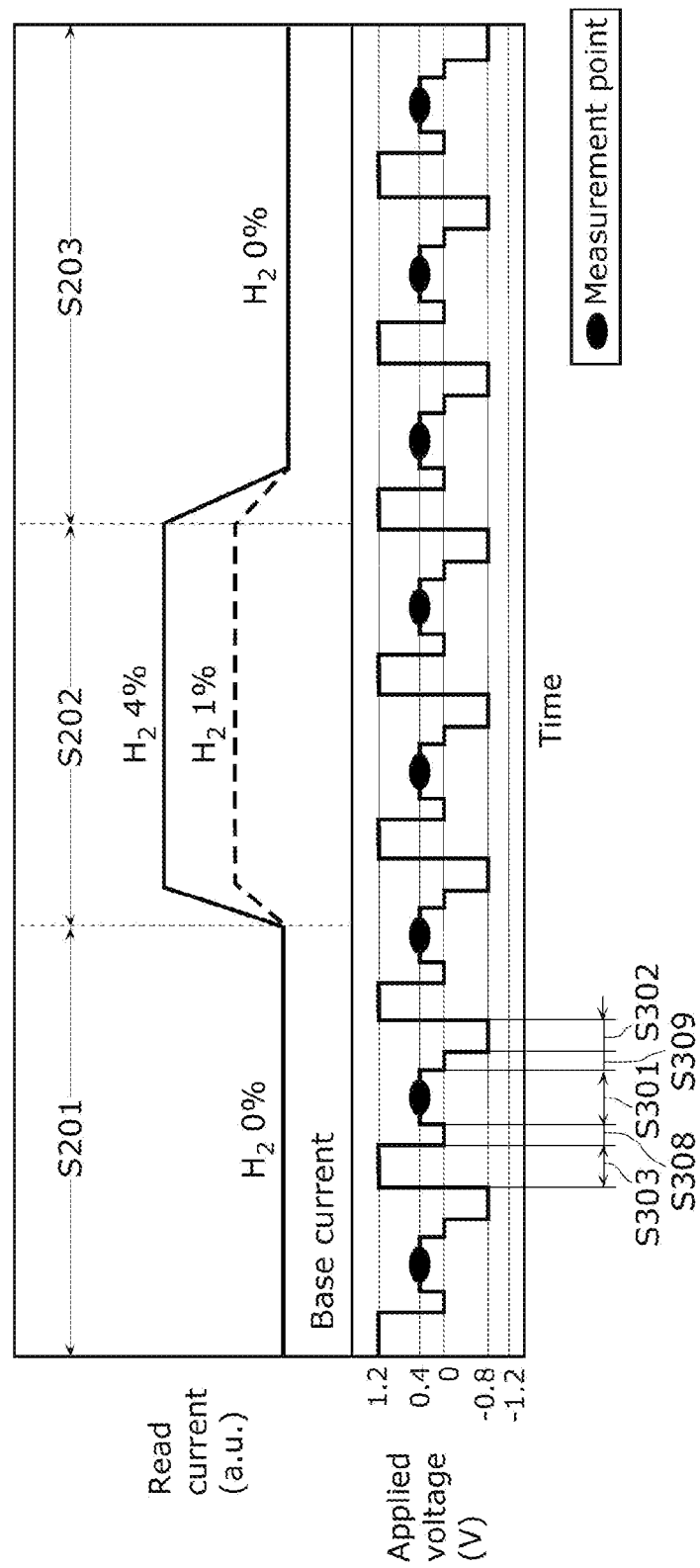
FIG. 17 is a diagram illustrating an example of a method for driving a gas sensor according to Embodiment 4.

FIG. 17 is a diagram illustrating an example of the driving method of gas sensor 200 according to Embodiment 4. FIG. 17 illustrates an applied voltage and a read current across first electrode 103 and second electrode 106 in gas sensor 200, using the same representation method as that used in FIG. 7A.

In the driving method according to Embodiment 4, a first positive voltage, a second positive voltage, and a negative voltage are repeatedly applied in this order (steps S303, S301, and S302), as illustrated in FIG. 17. A state in which no voltage is applied (i.e., the voltage applied across first electrode 103 and second electrode 106 is 0 V) is present between the application of the first positive voltage and the application of the second positive voltage that follows the application of the first positive voltage (step S308). The state in which no voltage is applied is also present between the application of the second positive voltage and the application of the negative voltage that follows the application of the second positive voltage (step S309). A single positive voltage pulse is applied in a single application of the first positive voltage, and a single negative voltage pulse is applied in a single application of the negative voltage.

Under the same circumstances as in the reference example, a read current was measured while a voltage was applied in accordance with the driving method according to Embodiment 4. The read current in FIG. 17 schematically illustrates the result of the measurement. FIG. 17 shows that it is possible, even with the driving method according to Embodiment 4, to bring back, to the base current, the value of the read current after the detection of hydrogen-containing gas, to stably detect hydrogen-containing gas with a simple procedure that does not require any conditional judgment.

Although the above description has illustrated an example in which a first positive voltage, a second positive voltage, and a negative voltage are 1.2 V, 0.4 V, and −0.8 V, respectively, the present disclosure is not limited to this example. An appropriate voltage such that the absolute value of an applied voltage in the application of the first positive voltage is smaller than the absolute value of the aforementioned initial break voltage and is larger than the absolute value of an applied voltage in the application of the negative voltage is used for the first positive voltage. An appropriate voltage such that the absolute value of an applied voltage in the application of the second positive voltage is smaller than the absolute value of an applied voltage in the application of the first positive voltage is used for the second positive voltage. Moreover, the waveforms of the first positive voltage and the negative voltage are not limited to square waves, and appropriate waveforms are used. Accordingly, the same effects can be obtained since the aforementioned mechanism of the resistance change phenomenon works. In addition, the same effects can be obtained even with gas detection device 802 that implements the driving method according to Embodiment 4.

Gas Sensor Driving Method According to Embodiment 5

Figure 18:
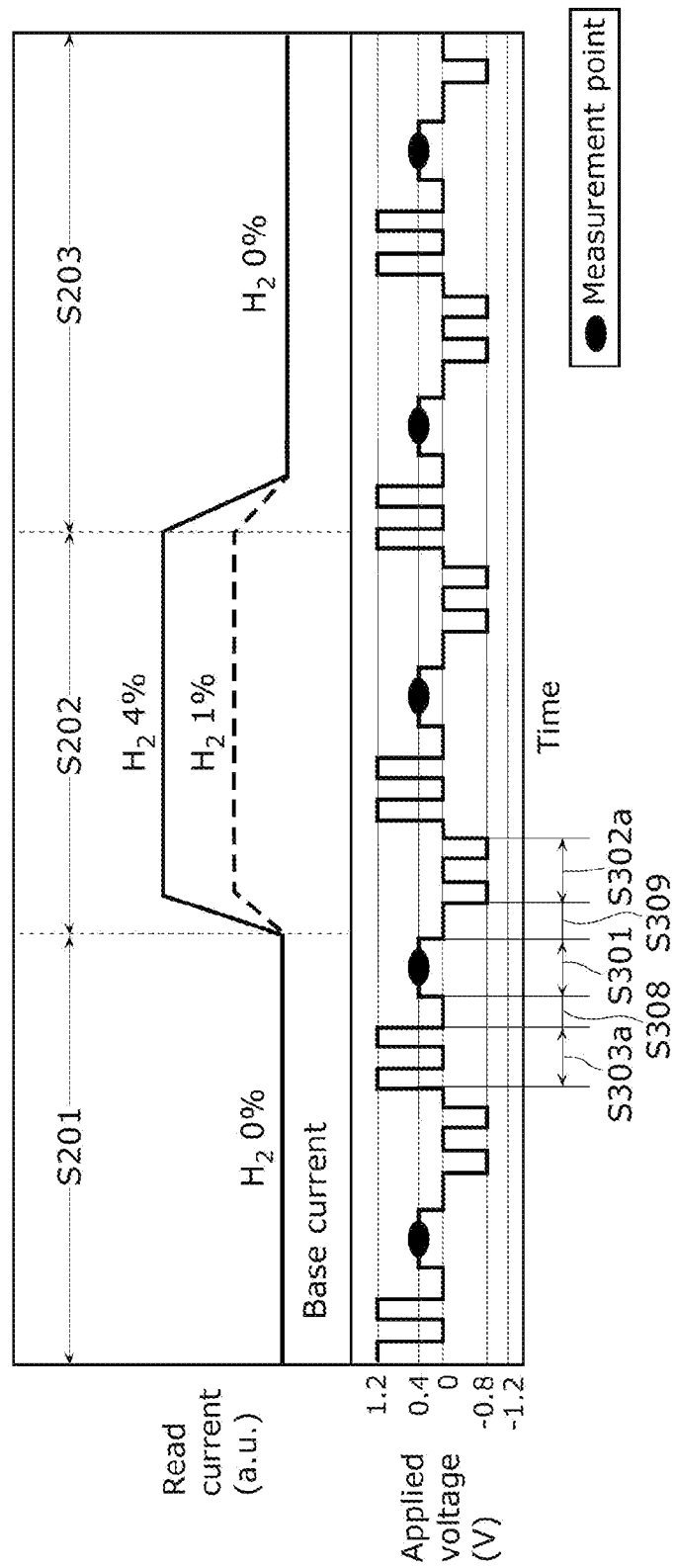
FIG. 18 is a diagram illustrating an example of a method for driving a gas sensor according to Embodiment 5.

A method for driving gas sensor 200 according to Embodiment 5 is implemented by gas detection device 802 illustrated in FIG. 18.

FIG. 18 is a diagram illustrating an example of the driving method of gas sensor 200 according to Embodiment 5. FIG. 18 illustrates an applied voltage and a read current across first electrode 103 and second electrode 106 in gas sensor 200, using the same representation method as that used in FIG. 7A.

In the driving method according to Embodiment 5, a first positive voltage, a second positive voltage, and a negative voltage are repeatedly applied in this order (steps S303a, S301, and S302a), as illustrated in FIG. 18. Two positive voltage pulses are applied in a single application of the first positive voltage, and two negative voltage pulses are applied in a single application of the negative voltage. A state in which no voltage is applied (i.e., the voltage applied across first electrode 103 and second electrode 106 is 0 V) is present between the application of the first positive voltage and the application of the second positive voltage that follows the application of the first positive voltage (step S308). The state in which no voltage is applied is also present between the application of the second positive voltage and the application of the negative voltage that follows the application of the second positive voltage (step S309).

Under the same circumstances as in the reference example, a read current was measured while a voltage was applied in accordance with the driving method according to Embodiment 5. The read current in FIG. 18 schematically illustrates the result of the measurement. FIG. 18 shows that it is possible, even with the driving method according to Embodiment 5, to bring back, to the base current, the value of the read current after the detection of hydrogen-containing gas, to stably detect hydrogen-containing gas with a simple procedure that does not require any conditional judgment.

Although the above description has illustrated an example in which a first positive voltage, a second positive voltage, and a negative voltage are 1.2 V, 0.4 V, and −0.8 V, respectively, the present disclosure is not limited to this example. An appropriate voltage such that the absolute value of an applied voltage in the application of the first positive voltage is smaller than the absolute value of the aforementioned initial break voltage and is larger than the absolute value of an applied voltage in the application of the negative voltage is used for the first positive voltage. An appropriate voltage such that the absolute value of an applied voltage in the application of the second positive voltage is smaller than the absolute value of an applied voltage in the application of the first positive voltage is used for the second positive voltage. Moreover, the waveforms of the first positive voltage and the negative voltage are not limited to square waves, and appropriate waveforms are used. Three or more positive voltage pulses may be applied in a single application of the first positive voltage and three or more negative voltage pulses may be applied in a single application of the negative voltage. Accordingly, the same effects can be obtained since the aforementioned mechanism of the resistance change phenomenon works. In addition, the same effects can be obtained even with gas detection device 802 that implements the driving method according to Embodiment 5.

SUMMARY OF THE EMBODIMENTS

A gas sensor driving method according to an aspect of the present disclosure is a gas sensor driving method for a gas sensor that (i) includes: a first electrode including a first principal surface; a second electrode including a second principal surface; a metal-oxide layer interposed between the first principal surface and the second principal surface that face each other; and an insulating film covering the first electrode, the metal-oxide layer, and the second electrode, and exposing at least a part of a third principal surface of the second electrode, the third principal surface being disposed on an opposite side of the second principal surface, and (ii) detects hydrogen in accordance with a change in a resistance value of the metal-oxide layer occurring when the part of the third principal surface contacts gas including gas molecules containing hydrogen atoms in a state in which a voltage is applied across the first electrode and the second electrode. The gas sensor driving method includes repeatedly applying a positive voltage and a negative voltage across the first electrode and the second electrode.

In the gas sensor driving method, the repeated applying of the positive voltage and the negative voltage may be performed at all times regardless of whether or not the gas molecules are present in the gas that contacts the part of the third principal surface.

In the gas sensor driving method, the resistance value of the metal-oxide layer may decrease when the part, which is exposed, of the third principal surface contacts the gas including the gas molecules containing the hydrogen atoms in the state in which the voltage is applied across the first electrode and the second electrode.

In the gas sensor driving method, when the positive voltage is applied, one or more positive voltage pulses may be applied.

In the gas sensor driving method, when the negative voltage is applied, one or more negative voltage pulses may be applied.

In the gas sensor driving method, when the one or more positive voltage pulses are applied, a value of a current flowing across the first electrode and the second electrode may be read out.

In the gas sensor driving method, an absolute value of an applied voltage in the application of the positive voltage may be larger than an absolute value of an applied voltage in the application of the negative voltage.

In the gas sensor driving method, a state in which no voltage is applied across the first electrode and the second electrode may be present (i) between the application of the positive voltage and the application of the negative voltage that follows the application of the positive voltage or (ii) between the application of the negative voltage and the application of the positive voltage that follows the application of the negative voltage.

The gas sensor driving method, when the positive voltage may be applied, a first positive voltage and a second positive voltage are applied, and an absolute value of an applied voltage in the application of the first positive voltage may be larger than an absolute value of an applied voltage in the application of the second positive voltage.

In the gas sensor driving method, the application of the second positive voltage may be performed after the application of the first positive voltage and before the application of the negative voltage that follows the application of the first positive voltage.

In the gas sensor driving method, the application of the second positive voltage is performed after the application of the negative voltage and before the application of the first positive voltage that follows the application of the negative voltage.

In the gas sensor driving method, the absolute value of the applied voltage in the application of the second positive voltage may be smaller than an absolute value of an applied voltage in the application of the negative voltage.

Accordingly, it is possible to achieve a gas sensor driving method that enables the repetition of the reading and resetting of the resistance value of the metal-oxide layer with a simple procedure, which does not require any conditional judgment, of repeatedly applying a positive voltage and a negative voltage across the first electrode and the second electrode.

A gas detection device according to an aspect of the present disclosure includes: a gas sensor that includes a first electrode including a first principal surface, a second electrode including a second principal surface, a metal-oxide layer interposed between the first principal surface and the second principal surface that face each other, an insulating film covering the first electrode, the metal-oxide layer, and the second electrode, and exposing at least a part of a third principal surface of the second electrode, the third principal surface being disposed on an opposite side of the second principal surface; and a power circuit that repeatedly applies a positive voltage and a negative voltage across the first electrode and the second electrode in the gas sensor.

The power circuit may include a voltage pulse generator circuit.

The gas detection device may further include: a measurement circuit that measures a resistance value of the gas sensor.

Accordingly, it is possible to achieve a gas detection device capable of repeating the reading and resetting of the resistance value of the metal-oxide layer with a simple procedure, which does not require any conditional judgment, of repeatedly applying a positive voltage and a negative voltage across the first electrode and the second electrode.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The gas sensor driving method and the gas detection device according to the present disclosure can be widely utilized for, for example, the detection of hydrogen-containing gas leaks.

The invention claimed is:

1. A gas sensor driving method for a gas sensor that (i) includes:
   a first electrode including a first principal surface;
   a second electrode including a second principal surface;
   a metal-oxide layer interposed between the first principal surface and the second principal surface that face each other; and
   an insulating film covering the first electrode, the metal-oxide layer, and the second electrode, and exposing at least a part of a third principal surface of the second electrode, the third principal surface being disposed on an opposite side of the second principal surface, and
   (ii) detects hydrogen in accordance with a change in a resistance value of the metal-oxide layer occurring when the part of the third principal surface contacts gas including gas molecules containing hydrogen atoms in a state in which a voltage is applied across the first electrode and the second electrode,
   the gas sensor driving method comprising:
   repeats firstly applying a positive voltage and subsequently applying a negative voltage across the first electrode and the second electrode.

2. The gas sensor driving method according to claim 1, wherein the repeated applying of the positive voltage and the negative voltage is performed at all times regardless of whether or not the gas molecules are present in the gas that contacts the part of the third principal surface.

3. The gas sensor driving method according to claim 1, wherein the resistance value of the metal-oxide layer decreases when the part, which is exposed, of the third principal surface contacts the gas including the gas molecules containing the hydrogen atoms in the state in which the voltage is applied across the first electrode and the second electrode.

4. The gas sensor driving method according to claim 1, wherein when the positive voltage is applied, one or more positive voltage pulses are applied.

5. The gas sensor driving method according to claim 1, wherein when the negative voltage is applied, one or more negative voltage pulses are applied.

6. The gas sensor driving method according to claim 4, wherein when the one or more positive voltage pulses are applied, a value of a current flowing across the first electrode and the second electrode is read out.

7. The gas sensor driving method according to claim 1, wherein an absolute value of an applied voltage in the application of the positive voltage is larger than an absolute value of an applied voltage in the application of the negative voltage.

8. The gas sensor driving method according to claim 1, wherein a state in which no voltage is applied across the first electrode and the second electrode is present (i) between the application of the positive voltage and the application of the negative voltage, the application of the negative voltage following the application of the positive voltage or (ii) between the application of the negative voltage and the application of the positive voltage, the application of the positive voltage following the application of the negative voltage.

9. The gas sensor driving method according to claim 1, wherein
   when the positive voltage is applied, a first positive voltage and a second positive voltage are applied, and
   an absolute value of an applied voltage in the application of the first positive voltage is larger than an absolute value of an applied voltage in the application of the second positive voltage.

10. The gas sensor driving method according to claim 9, wherein the application of the second positive voltage is performed after the application of the first positive voltage and before the application of the negative voltage, the application of the negative voltage following the application of the first positive voltage.

11. The gas sensor driving method according to claim 9, wherein the application of the second positive voltage is performed after the application of the negative voltage and before the application of the first positive voltage, the application of the first positive voltage following the application of the negative voltage.

12. The gas sensor driving method according to claim 9, wherein the absolute value of the applied voltage in the application of the second positive voltage is smaller than an absolute value of an applied voltage in the application of the negative voltage.

13. A gas detection device, comprising:
a gas sensor that includes:
   a first electrode including a first principal surface,
   a second electrode including a second principal surface,
   a metal-oxide layer interposed between the first principal surface and the second principal surface that face each other,
   an insulating film covering the first electrode, the metal-oxide layer, and the second electrode, and exposing at least a part of a third principal surface of the second electrode, the third principal surface being disposed on an opposite side of the second principal surface; and
a power circuit that repeats firstly applying a positive voltage and subsequently applying a negative voltage across the first electrode and the second electrode in the gas sensor.

14. The gas detection device according to claim 13, wherein the power circuit includes a voltage pulse generator circuit.

15. The gas detection device according to claim 13, further comprising:
a measurement circuit that measures a resistance value of the gas sensor.

* * * * *